United States Patent
Young et al.

(10) Patent No.: US 10,071,129 B2
(45) Date of Patent: Sep. 11, 2018

(54) METHOD FOR IDENTIFYING BROMODOMAIN INHIBITORS

(75) Inventors: Richard A. Young, Weston, MA (US);
Peter B. Rahl, Natick, MA (US);
James Bradner, Weston, MA (US)

(73) Assignee: WHITEHEAD INSTITUTE FOR BIOMEDICAL RESEARCH DANA-FARBER CANCER INSTITUTE, INC., Boston, MA (US)

( * ) Notice: Subject to any disclaimer, the term of this patent is extended or adjusted under 35 U.S.C. 154(b) by 82 days.

(21) Appl. No.: 14/342,265

(22) PCT Filed: Aug. 30, 2012

(86) PCT No.: PCT/US2012/053173
§ 371 (c)(1),
(2), (4) Date: Sep. 2, 2014

(87) PCT Pub. No.: WO2013/033420
PCT Pub. Date: Mar. 7, 2013

(65) Prior Publication Data
US 2014/0371157 A1 Dec. 18, 2014

Related U.S. Application Data

(60) Provisional application No. 61/529,165, filed on Aug. 30, 2011.

(51) Int. Cl.
*G01N 33/50* (2006.01)
*A61K 38/02* (2006.01)
*A61K 31/7088* (2006.01)
*A61K 31/713* (2006.01)
*A61K 31/7105* (2006.01)
*A61K 31/551* (2006.01)
*C07K 16/00* (2006.01)

(52) U.S. Cl.
CPC ............ *A61K 38/02* (2013.01); *A61K 31/551* (2013.01); *A61K 31/7088* (2013.01); *A61K 31/713* (2013.01); *A61K 31/7105* (2013.01); *C07K 16/00* (2013.01); *G01N 33/5011* (2013.01); *G01N 2500/02* (2013.01); *G01N 2500/10* (2013.01)

(58) Field of Classification Search
CPC ........... G01N 33/5011; G01N 2500/10; G01N 2500/20; C12Q 1/6897
See application file for complete search history.

(56) References Cited

U.S. PATENT DOCUMENTS

| | | | |
|---|---|---|---|
| 8,476,260 B2 * | 7/2013 | Miyoshi et al. | 514/220 |
| 2004/0043378 A1 * | 3/2004 | Zhou | A61K 31/198 435/5 |
| 2010/0286127 A1 | 11/2010 | Miyoshi et al. | |

FOREIGN PATENT DOCUMENTS

WO WO 2009084693 A1 * 7/2009
WO WO 2013/033420 3/2013

OTHER PUBLICATIONS

Marculescu et al. Alternative end-joining in follicular lymphomas't(14;18) translocation. Leukemia, vol. 16, pp. 120-126, 2002.*
Guglielmi et al. Combination of 3' and 5' IgH regulatory elements mimics the B-specific endogenous expression pattern of IgH genes from pro-B cells to mature B cells in a transgenic mouse model. Biochemica et Biophysica Acta, vol. 1642, pp. 181-190, 2003.*
Henseler et al. Diverse chemicals including aryl hydrocarbon receptor ligands modulate transcriptional activity of the 3' immunoglobulin heavy chain regulatory regions. Toxicology, vol. 261, pp. 9-18, 2009.*
Karlsson et al. Biosensor analysis of drug-target interactions: Direct and competitive binding assays for investigation of interactions between thrombin and thrombin inhibitors. Analytical Biochemistry, vol. 278, pp. 1-13, 2000.*
Wei et al. Therapeutic targeting of BET protein BRD4 delays murine lupus. International Immunopharmacology, http://dx.doi.org/10.1016/j.intimp.2015.10.036, 2015, printed as pp. 1/6-6/6.*
Nicodeme et al. Suppression of inflmmation by a synthetic histone mimic. Nature, vol. 468, pp. 1119-1123, Dec. 2010.*
Ide et al. Repair and biochemical effects of DNA-protein crosslinks. Mutation Research, vol. 711, pp. 113-122, 2011.*
Tretyakova et al. DNA-protein cross-links: Formation, structural identities, and biological outcomes. Accounts of Chemical Research, vol. 48, No. 6, pp. 1631-1644, 2015.*
Filippakopoulos, et al., "Selective inhibition of BET bromodomains", *Nature*, 468(7327); 1067-1073; 2010.

(Continued)

*Primary Examiner* — Jennifer Ann Dunston
(74) *Attorney, Agent, or Firm* — Lisa M. Warren, Esq.; Morse, Barnes-Brown & Pendleton, P.C.

(57) ABSTRACT

Disclosed herein are methods and compositions useful for inhibiting interaction between a bromodomain protein and an immunoglobulin (Ig) regulatory element. The methods and compositions are particularly useful for downregulating expression of an oncogene translocated with an Ig locus, as well as for treating a cancer (e.g., hematological malignancy) characterized by increased expression of an oncogene which is translocated with an Ig locus. Also disclosed herein are methods and assays for identifying agents that interfere with binding of bromodomain proteins to Ig regulatory elements, as well as methods and assays for identifying inhibitors of bromodomain.

6 Claims, 2 Drawing Sheets
(2 of 2 Drawing Sheet(s) Filed in Color)
Specification includes a Sequence Listing.

(56) References Cited

OTHER PUBLICATIONS

Garrett, et al., "Chromatin architecture near a potential 3' end of the Igh locus involves modular regulation of histone modifications during B-Cell development and in vivo occupancy at CTCF sites", *Molecular and Cellular Biology*, 4, 1511-1525; 2005.

Gostissa, et al., "Long-range oncogenic activation of IgH/c-myc translocations by the IgH 3' regulatory region", *Nature*, 462(7274), 803-807; 2009.

Jain, et al., "Variable IgH chain enhancer activity in Burkitt's lymphomas suggests an additional, direct mechanism of c-myc deregulation", *J. Immunol.*, 150(12):5418-28: 1993, Abstract only.

Zuber, et al., "RNAi screen identifies Brd4 as a therapeutic target in acute myeloid leukaemia", *Nature*, 478(7370), pp. 542-548. Abstract only, 2011.

Chesi, et al., "Frequent Dysregulation of the c-maf Proto-Oncogene at 16q23 by Translocation to an Ig Locus in Multiple Myeloma", *Blood*, 91: 4457-4463 (1998).

Einerson, et al., "Novel FISH probes designed to detect IGK-MYC and IGL-MYC rearrangements in B-cell lineage malignancy identify a new breakpoint cluster region designated BVR2", *Leukemia*, 20: 1790-1799 (2006).

Hideshima, et al., "Advances in biology of multiple myeloma: clinical applications", *Blood*, 104: 607-618 (2004).

Kuppers, et al., "Mechanisms of chromosomal translocations in B cell lymphomas" *Oncogene*, 20: 5580-5594 (2001).

International Search Report for International Application PCT/US2012/053173, dated Oct. 31, 2012.

* cited by examiner

METHOD FOR IDENTIFYING BROMODOMAIN INHIBITORS

RELATED APPLICATION(S)

This application is a national stage filing under 35 U.S.C. 371 of International Application No. PCT/US2012/053173, filed Aug. 30, 2012, which claims priority to and the benefit of U.S. Provisional Application No. 61/529,165, filed on Aug. 30, 2011, The entire teachings of the above application(s) are incorporated herein by reference. International Application PCT/US2012/053173 was published under PCT Article 21(2) in English.

GOVERNMENT SUPPORT

This invention was made with government support under NIH-1R01HG002668 awarded by the National Institutes of Health. The government has certain rights in the invention.

BACKGROUND OF THE INVENTION

Oncogenes are a group of genes which, when activated, can cause cancer. Most normal cells undergo a programmed form of death (apoptosis); activated oncogenes can cause those cells that ought to die to survive and proliferate instead. Most oncogenes require an additional step, such as mutations in another gene or exposure to environmental factors, to cause cancer. One method of oncogenesis occurs by the process of translocation, in which a segment of the chromosome breaks off and attaches to another chromosome. If the dislocated chromosome contains an oncogene, it may be removed from its usual regulatory controls and be continuously produced, thereby destabilizing the delicate balance of the mechanisms of cell growth. Many leukemias and lymphomas are caused by translocations of oncogenes. Since the 1970s, dozens of oncogenes have been identified in human cancer.

MYC is an oncogene overexpressed in 30% of all human cancers, and in many cancers it correlates with poor clinical outcome and increased chance of relapse [1]. c-Myc links growth factor stimulation and cell proliferation [2, 3]. Mitogenic growth factor signaling induces MYC expression. c-Myc, a basic helix-loop-helix leucine zipper transcription factor, forms heterodimers with Max to positively regulate transcription of proliferation-associated genes which include genes involved in metabolism, protein synthesis and cell-cycle [2, 3]. Thus, growth factor signaling promotes cell proliferation through inducing c-Myc's function in regulating transcription of proliferation-associated genes.

Myc is an attractive target for cancer therapy, as it is overexpressed in many human cancers that are difficult to treat and its expression is limited to proliferating cells. Studies in transgenic mouse models suggest that inactivation of MYC causes tumor regression through tumor cell differentiation or apoptosis [15-20]. In some models, such as the mouse osteosarcoma model, brief MYC inactivation significantly improved survival rates [19]. It has been suggested that the brief inactivation might induce an epigenetic change in the tumor cells such that reactivation would not necessarily cause tumor reformation. These studies also revealed that a wide variety of tumors depend on c-Myc function to maintain their tumorigenic state [15-20].

In most cancers, MYC overexpression correlates with poor clinical outcome, aggressiveness and advanced stage of cancer [1, 21]. Additionally, MYC overexpression correlates with an increased proliferative capacity. Importantly, MYC overexpression correlates with lack of response to chemotherapy and increases the probability of relapse in many cancers [1]. Developing therapies targeting the c-Myc regulatory pathway would greatly improve the therapeutic options for these aggressive, refractory malignancies.

SUMMARY OF THE INVENTION

The present invention relates to novel methods and compositions useful for inhibiting the interaction between a bromodomain protein and an immunoglobulin (Ig) regulatory element. The methods and compositions are particularly useful for downregulating the expression of an oncogene which is translocated with an Ig locus, as well as for treating a cancer (e.g., hematological malignancy) characterized by increased expression (e.g., overexpression) of an oncogene which is translocated with an Ig locus. Also disclosed herein are methods and assays for identifying agents that interfere with the binding of bromodomain proteins to Ig regulatory elements, as well as methods and assays for identifying inhibitors of bromodomain proteins.

Disclosed is a method of inhibiting interaction between a bromodomain protein and an immunoglobulin (Ig) regulatory element comprising contacting said bromodomain protein with an effective amount of an inhibitor of said bromodomain protein.

Also disclosed is a method for downregulating expression of an oncogene translocated with an Ig locus comprising contacting said locus with an effective amount of an inhibitor of a bromodomain protein.

Also disclosed is a method for treating a cancer comprising (a) determining the level of expression of an oncogene translocated with an Ig locus in a sample obtained from an individual having or suspected of having said cancer, wherein overexpression of said translocated oncogene in said sample in comparison with a control is indicative that said individual is an individual who would potentially benefit from treatment with an inhibitor of a bromodomain protein, and (b) administering an effective amount of said inhibitor to said individual if said translocated oncogene is overexpressed in said sample.

Also disclosed is a method for treating a cancer comprising administering an effective amount of an inhibitor of a bromodomain protein to an individual exhibiting overexpression of an oncogene translocated with an Ig locus.

Also disclosed is the use of a bromodomain inhibitor for the treatment of a cancer characterized by overexpression of an oncogene translocated with an Ig locus. In some embodiments use of the bromodomain inhibitor for the treatment of cancer characterized by overexpression of an oncogene translocated with an Ig locus is with the proviso that said oncogene is not c-Myc. In some embodiments use of the bromodomain inhibitor for the treatment of cancer characterized by overexpression of an oncogene translocated with an Ig locus is with the proviso that said cancer is not AML.

Also disclosed is a method for identifying an agent that interferes with binding of a bromodomain protein to an Ig regulatory element comprising (a) contacting a suitably conditioned cell containing a target gene under control of one or more Ig regulatory elements and a bromodomain protein which binds to said one or more Ig regulatory elements and activates expression of said target gene with a candidate agent, and (b) detecting expression of said target gene, wherein decreased expression of said target gene in the presence of said candidate agent as compared with expression of said target gene in the absence of said candidate agent is indicative of said agent's ability to interfere with binding of said bromodomain protein to said Ig regulatory element.

In some embodiments the method for identifying an agent that interferes with binding of a bromodomain protein to an Ig regulatory element further comprises the step of contacting said bromodomain protein immobilized onto a solid support with said candidate agent and a known inhibitor of said bromodomain protein, wherein said candidate agent's ability to outcompete said known inhibitor for binding to said bromodomain protein is indicative of said candidate agent's ability to interfere with binding of said bromodomain protein to said Ig regulatory element.

In some embodiments the method for identifying an agent that interferes with binding of a bromodomain protein to an Ig regulatory element further comprises the step of comparing a level of bromodomain protein occupancy at said Ig regulatory element in the presence of said candidate agent to a control, wherein decreased bromodomain protein occupancy at said Ig regulatory element in the presence of said candidate agent as compared to in the absence of said candidate agent is indicative of bromodomain inhibitor activity of said candidate agent.

In some embodiments the method for identifying an agent that interferes with binding of a bromodomain protein to an Ig regulatory element further comprises the steps of (c) contacting said bromodomain protein immobilized onto a solid support with said candidate agent and a known inhibitor of said bromodomain protein, wherein said candidate agent's ability to outcompete said known inhibitor for binding to said bromodomain protein is indicative of said candidate agent's ability to interfere with binding of said bromodomain protein to said Ig regulatory element, and (d) comparing a level of bromodomain protein occupancy at said Ig regulatory element in the presence of said candidate agent which is able to outcompete said known inhibitor to a control, wherein decreased bromodomain protein occupancy at said Ig regulatory element in the presence of said candidate agent as compared to in the absence of said candidate agent is indicative of bromodomain inhibitor activity of said candidate agent.

Disclosed also is a method for identifying an inhibitor of a bromodomain protein comprising (a) contacting a cell line expressing an oncogene translocated with an Ig locus with a candidate agent, (b) measuring the level of bromodomain protein occupancy at a regulatory element of said Ig locus, and (c) comparing said level of bromodomain occupancy at said regulatory element of said Ig locus to a control, wherein decreased bromodomain protein occupancy at said regulatory element of said Ig locus in the presence of the candidate agent as compared to in the absence of said candidate agent is indicative of bromodomain inhibitory activity of said candidate agent.

In some embodiments said Ig regulatory element is at an Ig locus on a chromosome.

In some embodiments downregulating expression of said oncogene comprises decreasing transcription of said oncogene. In some embodiments downregulating expression of said oncogene comprises decreasing the level or activity of an expression product of said oncogene.

In some embodiments said oncogene is overexpressed as a result of translocation with said Ig locus. In some embodiments said oncogene is not c-Myc. In some embodiments said oncogene is selected from the group consisting of Bcl2, Ccnd1, c-Maf, Pax5, Pim1, Bcl6, Irf4, Il3, Lyt10, Bcl3, and Malt1. In some embodiments said oncogene is c-Myc.

In some embodiments said Ig locus is selected from the group consisting of an IgH locus, an IgL locus, and an IgK locus.

In some embodiments said inhibitor interferes with binding of said bromodomain protein to an IgH regulatory element. In some embodiments said inhibitor interferes with binding of said bromodomain protein to a transcriptional start site of said oncogene. In some embodiments said inhibitor interferes with binding of said bromodomain protein to a transcriptional start site of an oncogene translocated with said Ig locus. In some embodiments said inhibitor interferes with acetyl-lysine recognition by a central hydrophobic cavity of said bromodomain protein. In some embodiments said inhibitor interferes with acetyl-lysine anchoring by a hydrogen bond of an asparagine residue of said bromodomain protein. In some embodiments said inhibitor inhibits binding of said bromodomain protein to an enhancer of said Ig locus. In some embodiments said inhibitor is selected from the group consisting of an antisense oligonucleotide, an aptamer, an intrabody, an oligopeptide, a ribozyme, an siRNA, a shRNA, and a small molecule.

In some embodiments said Ig regulatory element is an Ig enhancer.

In some embodiments said enhancer is an IgH enhancer. In some embodiments said enhancer is selected from the group consisting of E1, E2, E3 and E4.

In some embodiments said bromodomain protein is a BET bromodomain protein. In some embodiments said bromodomain protein is selected from the group consisting of Brd2, Brd3, Brd4, and BrdT.

In certain embodiments said oncogene is c-Myc, said Ig locus is an IgH locus, and said bromodomain protein is Brd4.

In some aspects said cancer is not AML. In some aspects said cancer is a hematological malignancy.

In some aspects said hematological malignancy is a leukemia, lymphoma or myeloma selected from the group consisting of acute lymphoblastic lymphoma (ALL), Burkitt's lymphoma, chronic lymphoid leukemia (CLL), diffuse large cell lymphoma, extranodal lymphoma, follicular lymphoma, lymphoplasmacytoid lymphoma, mantle zone lymphoma, monoclonal gammopathy of undetermined significance (MGUS), multiple myeloma, and mucosa-associated lymphatic tissue (MALT)-type lymphoma. In some aspects said hematological malignancy is acute myeloid leukemia (AML).

In certain embodiments said oncogene is bcl-1, said Ig locus is an IgH locus, and said cancer is mantle zone lymphoma. In certain embodiments said oncogene is bcl-2, said Ig locus is an IgH locus, and said cancer is follicular lymphoma. In certain embodiments said oncogene is bcl3, said Ig locus is an IgH locus, and said cancer is B-cell chronic lymphocytic leukemia. In certain embodiments said oncogene is bcl-6, said Ig locus is an IgH locus, and said cancer is diffuse large cell lymphoma. In certain embodiments said oncogene is bcl-9, said Ig locus is an IgH locus, and said cancer is acute lymphoblastic lymphoma. In certain embodiments said oncogene is bcl-10 and said cancer is mucosa-associated lymphatic tissue (MALT)-type lymphoma. In certain embodiments said oncogene is c-maf, said Ig locus is an IgH locus, and said cancer is multiple myleloma. In certain embodiments said oncogene is c-myc, said Ig locus is an IgH locus, and said cancer is Burkitt's lymphoma. In certain embodiments said oncogene is c-myc, said Ig locus is an IgH locus, and said cancer is multiple myeloma. In certain embodiments said oncogene is FGFR3, said Ig locus is an IgH locus, and said cancer is multiple myeloma. In certain embodiments said oncogene is Lyt-10, said Ig locus is an IgH locus, and said cancer is diffuse large cell lymphoma. In certain embodiments said oncogene is MUC1, said Ig locus is an IgH locus, and said cancer is extranodal lymphoma. In certain embodiments said oncogene is MUM1/IRF4, said Ig locus is an IgH locus, and said cancer is multiple myeloma. In certain embodiments said oncogene is Pax-5, said Ig locus is an IgH locus, and said cancer is lymphoplasmacytoid lymphoma.

In some aspects said inhibitor is an inhibitor of a BET bromodomain protein. In some aspects said inhibitor is an inhibitor of Brd4 protein. In some aspects said inhibitor is small molecule JQ1. In some aspects said inhibitor is administered with a pharmaceutically acceptable carrier. In some aspects said inhibitor is co-administered with at least one chemotherapeutic agent.

In some aspects said candidate agent interferes with acetyl-lysine recognition by a central hydrophobic cavity of said bromodomain protein or interferes with acetyl-lysine anchoring by a hydrogen bond of an asparagine residue of said bromodomain protein.

In some aspects said agent or candidate agent is selected from the group consisting of an antisense oligonucleotide, an aptamer, an intrabody, an oligopeptide, a ribozyme, an siRNA, a shRNA, and a small molecule.

In some aspects said Ig regulatory element is an IgH regulatory element.

In some aspects said target gene is a reporter gene. In some aspects said target gene is fused to a protein tag. In some aspects said protein tag is selected from the group consisting of a fluorescent peptide and a poly His tag. In some aspects said target gene is an oncogene which is translocated with an Ig locus. In some aspects said oncogene is not c-Myc.

In certain embodiments said bromodomain protein is Brd4, said oncogene is c-Myc, and said Ig regulatory element is an IgH enhancer.

In some embodiments said control bromodomain occupancy level is determined by contacting said cell line with a known bromodomain protein inhibitor, and measuring a level of bromodomain occupancy at said regulatory element of said Ig locus.

In some embodiments said known bromodomain protein inhibitor is small molecule JQ1.

In some embodiments said cell line is a multiple myeloma cell line. In some embodiments said Ig regulatory element is an IgH enhancer.

In some embodiments said step of measuring said level of bromodomain protein occupancy at said regulatory element of said Ig locus is performed using bromodomain protein ChIP-PCR analysis. In other embodiments, said step of measuring said level of bromodomain protein occupancy at said regulatory element of said Ig locus can be performed using sequencing techniques. In still other embodiments, said step of measuring said level of bromodomain protein occupancy at said regulatory element of said Ig locus can be performed using microarrays (e.g., a DNA microarray).

In some embodiments said ChIP-PCR analysis is performed using oligonucleotide primers complementary to at least a portion of a sequence of said regulatory element.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning: A Laboratory Manual*, $3^{rd}$ ed., Cold Spring Harbor Laboratory Press, Cold Spring Harbor, 2001; Harlow, E. and Lane, D., Antibodies A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; $10^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, available on the World Wide Web at subdomain ncbi.nlm.nih.gov/omim/ and in Online Mendelian Inheritance in Animals (OMIA), a database of genes, inherited disorders and traits in animal species (other than human and mouse), available on the World Wide Web at subdomain omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
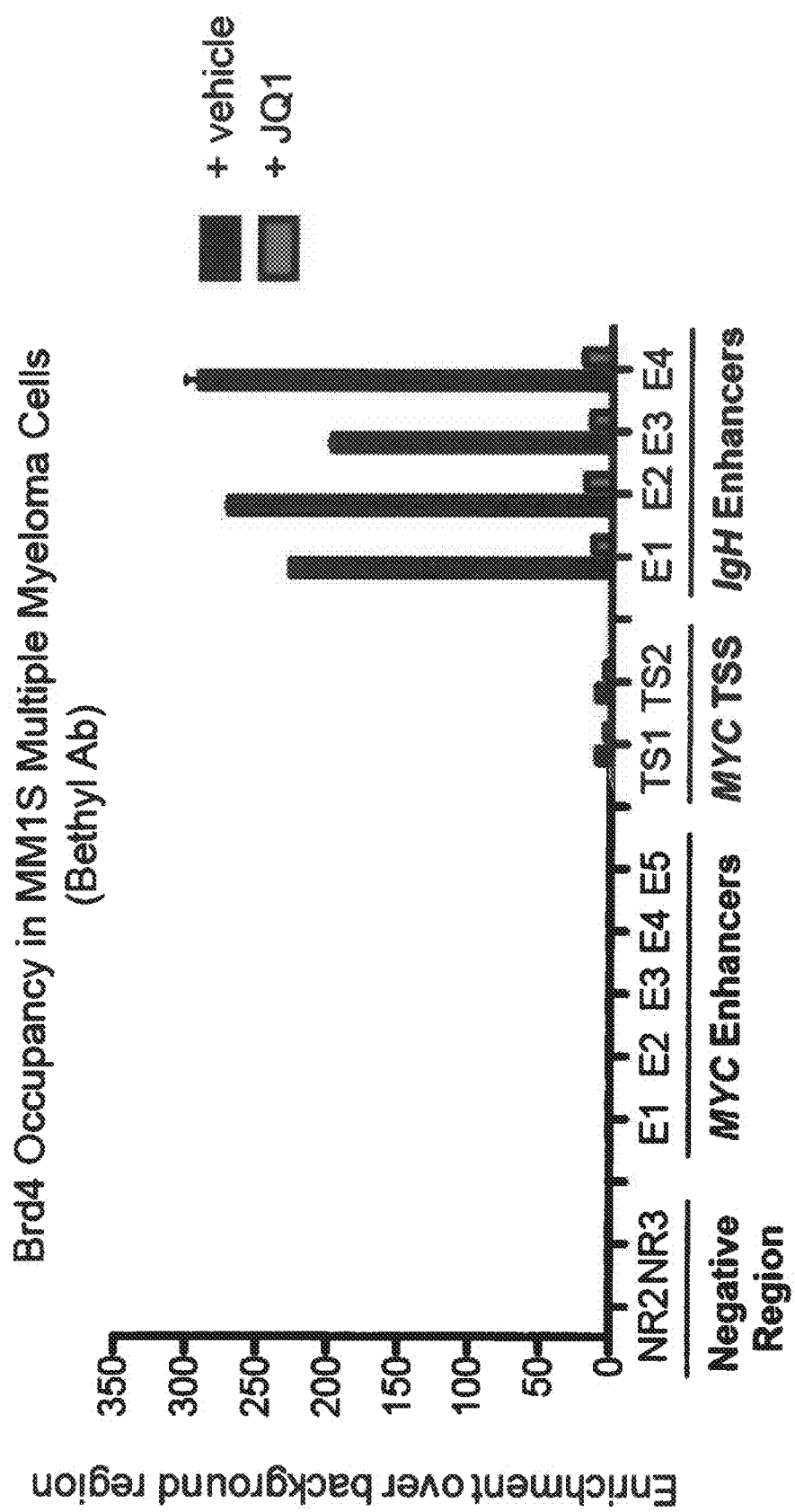
FIG. 1 illustrates that Brd4 binds the IGH regulator elements in IGH-MYC translocated multiple myeloma. Brd4 occupancy in MM1S cells at MYC enhancer regions, MYC TSS and IGH enhancer regions using two separate antibodies recognizing Brd4 (Bethyl).
Figure 2:
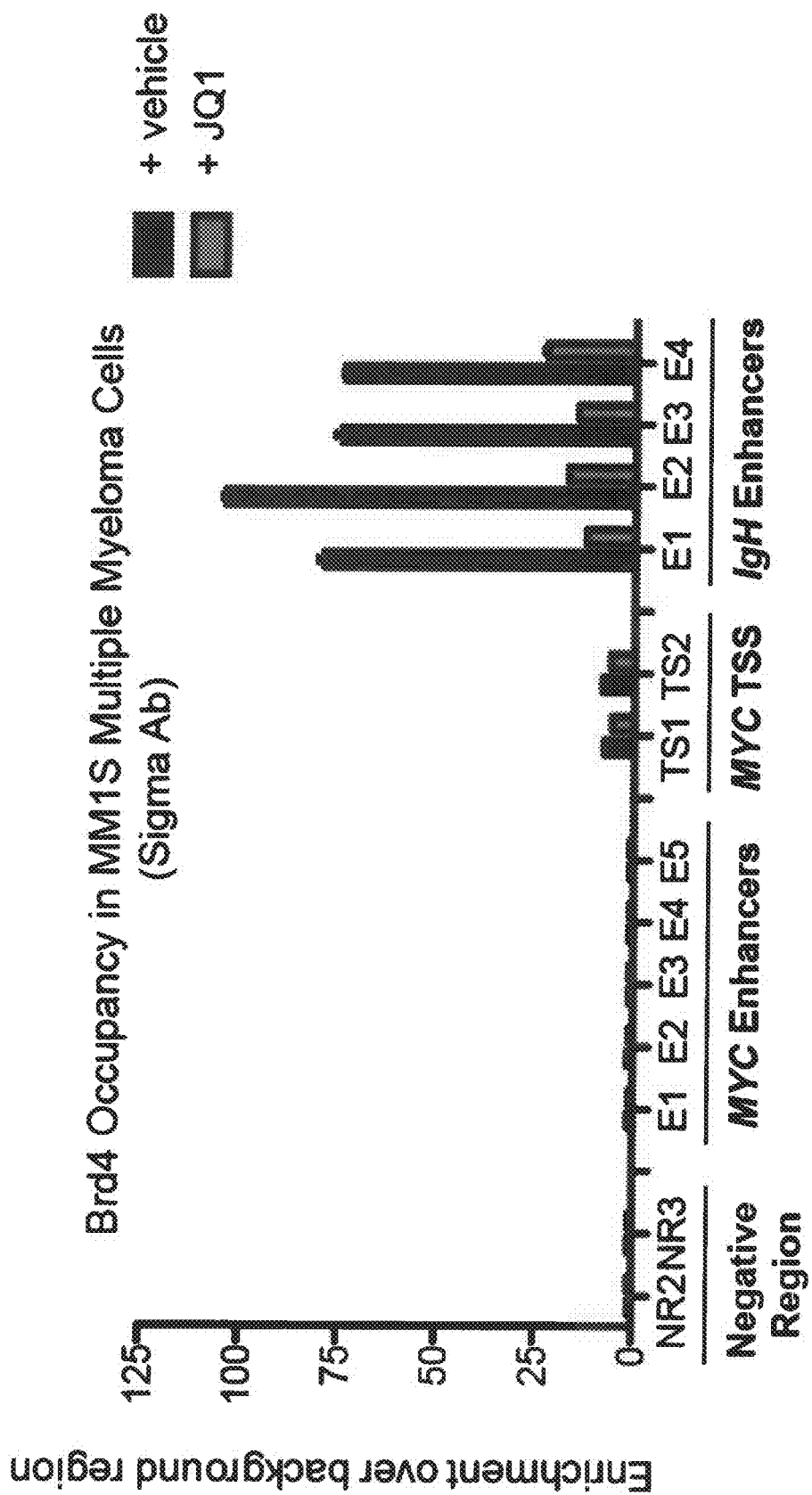
FIG. 2 shows that Brd4 binds the IGH regulator elements in IGH-MYC translocated multiple myeloma. Brd4 occupancy in MM1S cells at MYC enhancer regions, MYC TSS and IGH enhancer regions using two separate antibodies recognizing Brd4 (Sigma).

Described herein are novel methods, assays and compositions for the inhibition of bromodomain proteins as a mechanism to downregulate expression of oncogenes translocated with immunoglobulin (Ig) loci on chromosomes, and methods of identifying inhibitors of bromodomain proteins.

In particular, described herein is the discovery that bromodomain proteins bind to the immunoglobulin (Ig) regulatory elements of oncogenes translocated with Ig loci in a way that induces oncogene overexpression, and that bromodomain protein inhibitors interfere with bromodomain protein binding to such Ig regulatory elements to downregulate expression of such oncogenes translocated with Ig loci. The methods, assays and compositions disclosed herein also provide novel strategies for identifying bromodomain protein inhibitors that are useful for interfering with bromodomain protein binding to Ig regulatory elements.

Disclosed herein are methods for inhibiting the interaction between a bromodomain protein and an immunoglobulin (Ig) regulatory element, such methods comprising contacting said bromodomain protein with an effective amount of an inhibitor of said bromodomain protein. Bromodomain proteins refer to human proteins containing at least one bromodomain which mediates molecular recognition of acetyl-lysine in the aceylation of lysine residues on the tails of histones (which are typically correlated with an accessible chromatin structure and transcriptional activation) and non-histone proteins. Bromodomains generally share a conserved fold characterized by a left-handed bundle of four α-helices which are linked by regions of diverse loops that confer substrate specificity. The majority of bromodomains contain a central hydrophobic cavity that recognizes acetyl-lysine on the tails of histones and anchors acetyl-lysine via a hydrogen bond to a conserved asparagine residue in the binding pocket of the bromodomain. As used herein "bromodomain" or "bromodomain protein" refers to a polypeptide, whether wild-type or mutant, natural or synthetic, truncated or complete, or a variant thereof that possesses the minimum amino acid sequence sufficient for a functional bromodomain capable of mediating molecular recognition of acetyl-lysine of acetylated lysine residues on the tails of histones. Useful bromodomain proteins can include, for example, fusion proteins comprising a bromodomain and an additional portion having desired functionality (e.g., a reporter portion).

As used herein "contacting the cell" and the like, refers to any means of introducing an agent (e.g., nucleic acid, oligopeptide, ribozyme, intrabody, small molecule, etc.) into a target cell in vitro or in vivo, including by chemical and physical means, whether directly or indirectly or whether the agent physically contacts the cell directly or is introduced into an environment (e.g., culture medium) in which the cell is present or to which the cell is added. Contacting also is intended to encompass methods of exposing a cell, delivering to a cell, or 'loading' a cell with an agent by viral or non-viral vectors, and wherein such agent is bioactive upon delivery. The method of delivery will be chosen for the particular agent and use (e.g., cancer being treated). Parameters that affect delivery, as is known in the art, can include, inter alia, the cell type affected (e.g., tumor), and cellular location. In some embodiments, "contacting" includes administering the agent to an individual. In some embodiments, "contacting" refers to exposing a cell or an environment in which the cell is located to one or more bromodomain inhibitors of the present invention. In some embodiments, "contacting" refers to exposing a cell or an environment in which the cell is located to one or more candidate agents of the present invention.

As used herein an "effective amount" or "effective dose" of a compound or other agent (or composition containing such compound or agent) refers to the amount sufficient to achieve a desired biological and/or pharmacological effect, e.g., when delivered to a cell or organism according to a selected administration form, route, and/or schedule. As will be appreciated by those of skill in the art, the absolute amount of a particular compound, agent, or composition that is effective may vary depending on such factors as the desired biological or pharmacological endpoint, the agent to be delivered, the target tissue, etc. Those of skill in the art will further understand that an "effective amount" may be contacted with cells or administered in a single dose, or the desired effect may be achieved by use of multiple doses. An effective amount of a composition may be an amount sufficient to reduce the severity of or prevent one or more symptoms or signs of a disorder.

Also disclosed herein are methods for downregulating expression of an oncogene translocated with an Ig locus, such methods comprising contacting said locus with an effective amount of an inhibitor of a bromodomain protein. As used herein, "downregulating expression" refers to a reduction (measurable or observable) in the expression of a transcription or translation product of the oncogene in a target cell or cell population, or target tissue. In some embodiments, downregulating expression of the oncogene refers to decreasing the transcription of the oncogene. In some embodiments, downregulating expression of said oncogene comprises decreasing the level or activity of an expression product of said oncogene. As used herein "level" refers to a measure of the amount of or a concentration of a transcription product, for instance an mRNA, or a translation product, for instance a protein or polypeptide. As used herein "activity" refers to a measure of the ability of a transcription product or a translation product to produce a biological effect.

In some embodiments, the oncogene is overexpressed as a result of translocation with said Ig locus. As used herein "overexpression," "overexpressed" or "overexpression of an oncogene" are used interchangeably to refer to a level of expression (e.g., an amount of mRNA or protein produced, e.g., oncogene expression) or the amount of activity (e.g., bromodomain protein binding acetylated lysine residues) that is generally at least about 1, 2, 3, 4, 5, 6, 7, 8, 9, 10-fold or more higher than a reference or normal level and/or activity. However, modestly increased levels and/or activity, such as about 0.1, 0.2, 0.3, 0.4, 0.5, 0.6, 0.7, 0.8, 0.9-fold higher levels and/or activity than a reference or normal level or activity of an oncogene (e.g., an oncogene translocated with an Ig locus) or its expression are also encompassed by this phrase.

As described herein, any oncogene which is translocated with an Ig locus (e.g. an Ig heavy or Ig light locus) may be beneficially targeted by the methods disclosed herein. Such methods of inhibiting or downregulating the expression of translocated oncogene are useful for treating disorders characterized by expression, increased expression, or overexpression of such translocated oncogenes. Briefly, and without wishing to be bound by theory, it is believed that oncogene translocation with Ig loci places the translocated oncogene under control of the Ig regulatory elements, which can lead to increased expression or overexpression because such Ig loci are highly expressed in B- and T-cells. This causes increased expression or overexpression of the translocated oncogene and uncontrolled proliferation of the cell.

By way of non-limiting example, the oncogene can be one or more of Bcl2, Bcl3, Bcl6, Bcl9, Bcl10, Ccnd1, c-Maf, c-myc, Pax5, Pim1, Irf4, Il3, Lyt10, and Malt1. In certain embodiments the oncogene is not c-myc.

In one example, expression of oncogene c-myc translocated with an Ig locus can be downregulated by contacting the Ig locus with an effective amount of a bromodomain protein inhibitor as described herein. In one embodiment, overexpressed oncogene c-Myc translocated with an IgH locus can be inhibited or downregulated by contacting the IgH locus with an effective amount of a bromodomain inhibitor as described herein.

As another example, expression of oncogene Bcl2 translocated with an Ig locus can be downregulated by contacting the Ig locus with an effective amount of a bromodomain protein inhibitor as described herein. In one embodiment, overexpressed oncogene Bcl2 translocated with an IgH locus can be inhibited or downregulated by contacting the IgH locus with an effective amount of a bromodomain inhibitor as described herein.

In one embodiment, expression of oncogene Bcl3 translocated with an Ig locus can be downregulated by contacting the Ig locus with an effective amount of a bromodomain protein inhibitor according to methods described herein. For example, overexpressed oncogene Bcl3 translocated with an IgH locus can be inhibited or downregulated by contacting the IgH locus with an effective amount of a bromodomain inhibitor.

In another embodiment, expression of oncogene Bcl6 translocated with an Ig locus can be downregulated by contacting the Ig locus with an effective amount of a bromodomain protein inhibitor as described herein. In one embodiment, overexpressed oncogene Bcl6 translocated with an IgH locus can be inhibited or downregulated by contacting the IgH locus with an effective amount of a bromodomain inhibitor. In another embodiment, overexpressed oncogene Bcl6 translocated with an IgL locus can be inhibited or downregulated by contacting the IgL locus with an effective amount of a bromodomain inhibitor as described herein.

In a further embodiment, expression of oncogene Bcl9 translocated with an Ig locus can be downregulated by contacting the Ig locus with an effective amount of a bromodomain protein inhibitor. For example, overexpressed oncogene Bcl9 translocated with an IgH locus can be inhibited or downregulated by contacting the IgH locus with an effective amount of a bromodomain inhibitor.

In another embodiment, expression of oncogene Bcl10 translocated with an Ig locus (e.g., an IgH locus) can be downregulated by contacting the Ig locus with an effective amount of a bromodomain protein inhibitor. In one embodiment, overexpressed oncogene Bcl10 translocated with an IgH locus can be inhibited or downregulated by contacting the IgH locus with an effective amount of a bromodomain inhibitor as described herein.

In one embodiment, expression of oncogene Ccnd1 translocated with an Ig locus can be downregulated by contacting the Ig locus with an effective amount of a bromodomain protein inhibitor according to methods of the invention. In an embodiment, overexpressed oncogene Ccnd1 translocated with an IgH locus can be inhibited or downregulated by contacting the IgH locus with an effective amount of a bromodomain inhibitor.

In one embodiment, expression of oncogene c-Maf translocated with an Ig locus can be downregulated by contacting the Ig locus with an effective amount of a bromodomain protein inhibitor. In one embodiment, overexpressed oncogene c-Maf translocated with an IgH locus can be inhibited or downregulated by contacting the IgH locus with an effective amount of a bromodomain inhibitor.

In another example, expression of oncogene Pax5 translocated with an Ig locus can be downregulated by contacting the Ig locus with an effective amount of a bromodomain protein inhibitor of the present invention. In an embodiment, overexpressed oncogene Pax5 translocated with IgH locus can be inhibited or downregulated by contacting the IgH locus with an effective amount of a bromodomain inhibitor of the present invention.

In one embodiment, expression of oncogene Pim1 translocated with Ig locus can be downregulated by contacting the Ig locus with an effective amount of a bromodomain protein inhibitor of the present invention. In an embodiment, overexpressed oncogene Pim1 translocated with IgH locus can be inhibited or downregulated by contacting the IgH locus with an effective amount of a bromodomain inhibitor of the present invention.

In one embodiment, expression of oncogene Irf4 translocated with Ig locus can be downregulated by contacting the Ig locus with an effective amount of a bromodomain protein inhibitor of the present invention. In an embodiment, overexpressed oncogene Irf4 translocated with IgH locus can be inhibited or downregulated by contacting the IgH locus with an effective amount of a bromodomain inhibitor of the present invention.

In one embodiment, expression of oncogene Il3 translocated with Ig locus can be downregulated by contacting the Ig locus with an effective amount of a bromodomain protein inhibitor of the present invention. In an embodiment, overexpressed oncogene Il3 translocated with IgH locus can be inhibited or downregulated by contacting the IgH locus with an effective amount of a bromodomain inhibitor of the present invention.

In one embodiment, expression of oncogene Lyt10 translocated with Ig locus can be downregulated by contacting the Ig locus with an effective amount of a bromodomain protein inhibitor of the present invention. In an embodiment, overexpressed oncogene Lyt10 translocated with IgH locus can be inhibited or downregulated by contacting the IgH locus with an effective amount of a bromodomain inhibitor of the present invention.

In one embodiment, expression of oncogene Malt translocated with Ig locus can be downregulated by contacting the Ig locus with an effective amount of a bromodomain protein inhibitor of the present invention. In an embodiment, overexpressed oncogene Malt1 translocated with IgH locus can be inhibited or downregulated by contacting the IgH locus with an effective amount of a bromodomain inhibitor of the present invention.

In one embodiment, the oncogene is c-Myc. For example, expression of oncogene c-Myc translocated with Ig locus can be downregulated by contacting the Ig locus with an effective amount of a bromodomain protein inhibitor of the present invention. In another example, overexpressed oncogene c-Myc with IgH locus can be inhibited or downregulated by contacting the IgH locus with an effective amount of a bromodomain inhibitor of the present invention. In an embodiment, overexpressed oncogene c-Myc translocated with IgL locus can be inhibited or downregulated by a contacting the IgL locus with an effective amount of a bromodomain inhibitor of the present invention.

It should be appreciated by those skilled in the art that any Ig locus with which an oncogene can be translocated may result in overexpression of the translocated oncogene. In such instances, the bromodomain protein inhibitors and methods for inhibiting or downregulating translocated oncogene expression disclosed herein may be advantageously employed. In certain embodiments, the Ig locus is selected from the group consisting of an IgH locus, an IgL locus, and an IgK locus.

In one embodiment, the Ig locus in which a translocation occurs is the IgH locus. The human IgH locus is located on the chromosome 14 at band 14q32.33, adjacent to the telomeric extremity of the long arm. The human IgH locus at 14q32.33 spans 1250 kilobases (kb). It contains 123 to 129 IgHV genes, depending on the haplotypes, 27 IgHD segments which belong to 7 subgroups, 9 IgHJ segments, and 11 IgHC genes. The IgH locus encodes immunoglobulin heavy chains which result from the rearrangement of the IgHV, IgHD and IgHJ genes. Translocations involving the IgH locus may result from errors of recombinase enzyme complex (RAG1, RAG2, etc.), Ig and T-cell receptor V-J or V-D-J rearrangements, or switch enzymes.

In one embodiment, the Ig locus in which a translocation occurs is the IgL locus. The human IgL locus is located on the chromosome 22 on the long arm at band 22q11.2. The human IgL locus spans approximately 1050 kb and contains 29 to 32 functional IgLV genes which belong to 10 subgroups, 4 to 5 IgLJ, 4 to 5 IgLC functional genes in the 7-IgLC haplotype. The IgL locus encodes immunoglobulin lambda chains which result from the rearrangement of the IgLV, IgLJ genes with a deleted intermediate DNA region to produce a rearranged IgLV-J gene which is transcribed with a IgLC gene and translated to produce the Ig lambda chain. Translocations involving the IgH locus may result from errors of recombinase enzyme complex (RAG1, RAG2, etc.), or T-cell receptor V-J or V-D-J rearrangements.

In one embodiment, the Ig locus in which a translocation occurs is the IgK locus. The human IgK locus is located on the chromosome 2 on the short arm at band 2p11.2. The human IgK locus contains genes for the kappa light chains of immunoglobulins which are encoded by IgKV, IgKJ, and IgKC genes which undergo VDJ recombination events which may result in translocations with oncogenes.

In certain embodiments, the present invention contemplates methods of inhibiting the function, level, or activity of a bromodomain domain protein using one or more bromodomain inhibitor of the present invention. As used herein "bromodomain inhibitor", "inhibitor of bromodomain protein" and "bromodomain protein inhibitor" refer to inhibitors of bromodomain proteins, and in particular inhibitors which interfere with the ability of bromodomain proteins to interact with acetylated lysine residues residing on the tails of histones, including agents that inhibit the level and/or activity of bromodomain protein, or agents that downregulate transcription of a gene encoding a bromodomain protein. Those skilled in the art will appreciate that interference with the ability of a bromodomain protein to interact with acetylated lysines on histone tails may refer to preventing the bromodomain protein from recognizing or binding to the acetyl-lysine, competing with acetyl-lysine for hydrogen bonding to a conserved asparagine residue present in the central hydrophobic cavity or binding pocket of the bromodomain so as to displace the bromodomain protein from the chromatin, disrupting the hydrogen bond between acetyl-lysine and the conserved asparagine residue so as to displace the bromodomain protein from the acetyl-lysine motif, or any other means by which molecular recognition between acetyl-lysine and the bromodomain is disrupted preventing the bromodomain protein from contributing to the formation of a functional transcription factor complex and thereby modulating gene expression. In some embodiments, bromodomain protein inhibitors include molecules that bind directly to a functional region of a bromodomain protein. In certain embodiments, the bromodomain inhibitor interferes with binding of a bromodomain protein to an Ig regulatory element. In some embodiments, the bromodomain inhibitor interferes with binding of a bromodomain protein to an IgH regulatory element. In some embodiments, the bromodomain inhibitor interferes with binding of said bromodomain protein to a transcriptional start site of an oncogene. In certain embodiments, the bromodomain inhibitor interferes with binding of a bromodomain protein to a transcriptional start site of an oncogene translocated with an Ig locus. In some embodiments, the bromodomain inhibitor interferes with acetyl-lysine recognition by a central hydrophobic cavity of said bromodomain protein. In some embodiments, the bromodomain inhibitor interferes with acetyl-lysine anchoring by a hydrogen bond of an asparagines residue of a bromodomain protein. In such instances, the asparagines residue is a conserved residue which resides in a binding pocket or central hydrophobic pocket of the bromodomain protein.

In some embodiments, the present invention contemplates bromodomain inhibitors that interfere with the interaction between a bromodomain protein and an Ig regulatory element. It should be appreciated by those skilled in the art that the Ig regulatory element may be any regulatory element that is part of a functional Ig gene or Ig locus translocated with an oncogene. In some embodiments, the Ig regulatory element is an Ig enhancer. In such instances, the bromodomain inhibitor inhibits binding of the bromodomain protein to an enhancer of the Ig locus. In some embodiments, the enhancer is an IgH enhancer. In some embodiments, the enhancer is selected from the group consisting of E1, E2, E3 and E4. Ig enhancers E1, E2, E3 and E4 are described in further detail in Example 1 below. In some embodiments, the enhancer is a regulatory element having a nucleic acid sequence substantially complementary to or similar to an oligonucleotide sequence listed in Table 1. In some embodiments, the enhancer is a putative Ig enhancer. In other embodiments, the regulatory element comprises a nucleotide sequence adjacent to an Ig enhancer, a binding site within such nucleotide sequence, or a transcription factor which binds to such sequence.

It should be appreciated that any method or agent capable of inhibiting a bromodomain protein now known, or later discovered, can be used in accordance with the methods of the present invention to inhibit a bromodomain protein or to downregulate expression of an oncogene translocated with an Ig locus. Examples of such methods or agents known to those skilled in the art include, but are not limited to antisense oligonucleotides, oligopeptides, interfering RNA e.g., small interfering RNA (siRNA), small hairpin RNA (shRNA), aptamers, ribozymes, small molecule inhibitors, or intrabodies, and combinations thereof.

In certain embodiments, the bromodomain protein is a BET bromodomain protein. In such instances the bromodomain protein may include Brd2, Brd3, and Brd4. In one embodiment, the bromodomain protein is BrdT.

In one exemplary embodiment, bromodomain protein Brd4 binds to an IgH regulatory element that induces overexpression of oncogene c-Myc translocated with IgH locus. In such embodiment, contacting said c-Myc oncogene translocated with IgH locus with an effective amount of a bromodomain protein inhibitor of the present invention (e.g., a BET bromodomain inhibitor, e.g., a Brd4 inhibitor) may be advantageously performed to downregulate the expression of c-Myc translocated with IgH.

In another aspect, a method for treating a cancer is disclosed herein, such method comprising (a) determining the level of expression of an oncogene translocated with an Ig locus in a sample obtained from an individual having or suspected of having said cancer, wherein overexpression of said translocated oncogene in said sample in comparison with a control is indicative that said individual is an individual who would potentially benefit from treatment with an inhibitor of a bromodomain protein; and (b) administering an effective amount of said inhibitor to said individual if said translocated oncogene is overexpressed in said sample.

In yet another aspect, a method for treating a cancer comprises administering an effective amount of an inhibitor of a bromodomain protein to an individual exhibiting overexpression of an oncogene translocated with an Ig locus. In one embodiment, the cancer is not acute myeloid leukemia.

As used herein "treat", "treating" and similar terms refer to providing medical and/or surgical management of a subject. Treatment can include, but is not limited to, administering a compound or composition (e.g., a pharmaceutical composition or a composition comprising appropriate cells in the case of cell-based therapy) to a subject. Treatment is typically undertaken in an effort to alter the course of a disorder (which term is used to refer to a disease, syndrome, or abnormal condition) or undesirable or harmful condition in a manner beneficial to the subject. The effect of treatment can generally include reversing, alleviating, reducing severity of, delaying the onset of, curing, inhibiting the progression of, and/or reducing the likelihood of occurrence or reoccurrence of the disorder or condition, or one or more symptoms or manifestations of such disorder or condition. A composition can be administered to a subject who has developed a disorder or is at risk of developing a disorder (e.g., cancer, e.g., a hematological malignancy). A composition can be administered prophylactically, i.e., before development of any symptom or manifestation of a disorder. Typically in this case the subject will be at increased risk of developing the disorder relative to a member of the general population. For example, a composition can be administered to a subject with a risk factor, e.g., a translocation of an oncogene with an Ig locus, wherein the risk factor is associated with increased likelihood of developing the disorder but before the subject has developed symptoms or manifestations of the disorder. "Preventing" can refer to administering a composition to a subject who has not developed a disorder, so as to reduce the likelihood that the disorder will occur or so as to reduce the severity of the disorder should it occur. The subject may be identified (e.g., diagnosed by a medical practitioner) as having, suspected of having, or being at risk of developing the disorder (e.g., at increased risk relative to many most other members of the population or as having a risk factor that increases likelihood of developing the disorder).

As used herein determining or detecting the level of expression of a gene or oncogene (e.g., an oncogene translocated with Ig locus) refers to any method that can be used to detect the level of expression of a target gene, including mRNA levels and/or the activity or level of a protein encoded by that gene. Methods for determining the level of expression of a particular gene are well known in the art. Any such method now known or later developed can be used to determine or detect the levels of gene or oncogene expression in accordance with the methods disclosed herein. Examples of such suitable methods include RT-PCR, real-time PCR, Northern blotting, Western blotting, in situ hybridization, oligonucleotide arrays (e.g., microarray) or chips, to name more than a few. Such methods can be used to detect gene expression or overexpression of a gene (e.g., an oncogene translocated with an Ig locus)

As used herein "sample" or "biological sample" are used interchangeably to refer to a sample of biological tissue or fluid that contains nucleic acids or polypeptides, e.g., an oncogene translocated with an Ig locus. Such samples may include isolated tissues or sections of tissues such as biopsy or autopsy samples, frozen sections taken for histological purposes, blood, plasma, serum. A biological sample may also refer to transformed cell cultures derived from patient tissues. Those skilled in the art will appreciate that any methods now known, or later developed, for isolating, extracting, or obtaining a sample with sufficient measurable quanitites of nucleic acids or polypeptides can be used in accordance with the methods disclosed herein.

As used herein "administering" a bromodomain protein inhibitor or composition thereof may be performed according to any suitable method now known, or later developed, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Other therapeutic regimens may be combined with the administration of the bromodomain protein inhibitors. The combined administration may include co-administration, using separate formulations or a single pharmaceutical formulation, and consecutive administration in either order, wherein there may be a time period while both (or all) active agents simultaneously exert their biological activities. Such combined therapy may generate a synergistic therapeutic effect.

For the treatment of a cancer, the dosage and mode of administration will be chosen by the physician according to known criteria. A therapeutically effective dose of the bromodomain protein inhibitor alone, or linked to a cancer therapeutic agent, is the amount effective for inhibiting the binding of the bromodomain protein to an Ig regulatory element thereby downregulating expression of an oncogene translocated with an Ig locus. The dosage should not cause adverse side effects, such as unwanted cross-reactions, anaphylactic reactions, and the like. Generally, the dosage will vary with the age, condition, sex and route of administration, or whether other drugs are included in the regimen, and can be determined by one of skill in the art. The appropriate dosage of the bromodomain inhibitor will also depend on the type of cancer (e.g., leukemia, myeloma, lymphoma, etc.) to be treated and the severity and course of the disease. The bromodomain inhibitor may be appropriately administered to the patient at one time or over a series of treatments.

In some embodiments, the cancer to be treated according to the methods described herein is a hematological malignancy. As used herein, "blood cancer", "hematological malignancy", "hematological cancer", "hematopoietic malignancy" and "hematopoietic cancer" are used interchangeably to refer to diseases affecting the blood, bone marrow, and lymph nodes. In some embodiments, a hematological malignancy refers to a leukemia, a lymphoma or a myeloma and specific disease types thereof. Examples of such hematological malignancies include acute lymphoblastic lymphoma (ALL), Burkitt's lymphoma, chronic lymphoid leukemia (CLL), diffuse large cell lymphoma, extranodal lymphoma, follicular lymphoma, lymphoplasmacytoid lymphoma, mantle zone lymphoma, monoclonal gammopathy of undetermined significance (MGUS), multiple myeloma, and mucosa-associated lymphatic tissue (MALT)-type lymphoma. Other examples of hematological malignancies include Waldenstrom's macroglobulinemia, heavy chain disease, chronic myelogenous leukemia (CML), hairy cell leukemia, promyelocytic leukemia, myelomonocytic leukemia, monocytic leukemia, Hodgkin's lymphoma, non-Hodgkin's lymphoma (small-cell type, large-cell type, and mixed-cell type). In one embodiment, the hematological malignancy is acute myeloid leukemia (AML).

The methods of treating cancer disclosed herein relate to a variety of cancers characterized by abnormal expression (e.g., overexpression) of oncogenes translocated with Ig loci. It should be appreciated that any oncogene which is translocated with an Ig locus may exhibit abnormal expression (e.g., overexpression), and thus can be targeted for downregulation or inhibition as a therapeutic strategy for treating cancer with the bromodomain inhibitors disclosed herein or identified in accordance with the methods disclosed herein. In one embodiment, the oncogene is not c-Myc.

In one embodiment, the oncogene is bcl-1, the Ig locus is an IgH locus, and the cancer is mantle zone lymphoma. For example, patients having or suspected of having mantle zone lymphoma may exhibit oncogene bcl-2 translocated with an IgH locus. In some instances, oncogene bcl-2 translocated with an IgH locus may be overexpressed in such patients. The expression level of oncogene bcl-2 translocated with an IgH locus may be detected in such patients using known methods of measuring or detecting gene expression. Those patients in which oncogene bcl-2 translocated with an IgH locus is overexpressed may benefit from administration of an effective amount of a bromodomain protein inhibitor.

In one embodiment, the oncogene is bcl-2, the Ig locus is an IgH locus, and the cancer is follicular lymphoma. For example, patients having or suspected of having follicular lymphoma may exhibit oncogene bcl-2 translocated with an IgH locus. In some instances, oncogene bcl-2 translocated with an IgH locus may be overexpressed in such patients. The expression level of oncogene bcl-2 translocated with an IgH locus may be detected in such patients using known methods of measuring or detecting gene expression. Those patients in which oncogene bcl-2 translocated with an IgH locus is overexpressed may benefit from administration of an effective amount of a bromodomain protein inhibitor.

In one embodiment, the oncogene is bcl-3, the Ig locus is an IgH locus, and the cancer is B-cell chronic lymphocytic leukemia. For example, patients having or suspected of having B-cell chronic lymphocytic leukemia may exhibit oncogene bcl-3 translocated with an IgH locus. In some instances, oncogene bcl-3 translocated with an IgH locus may be overexpressed in such patients. The expression level of oncogene bcl-3 translocated with an IgH locus may be detected in such patients using known methods of measuring or detecting gene expression. Those patients having or suspected of having B-cell chronic lymphocytic leukemia in which oncogene bcl-3 translocated with an IgH locus is overexpressed may benefit from administration of an effective amount of a bromodomain protein inhibitor in accordance with the methods disclosed herein. In one embodiment, the bcl-3 oncogene translocation is a [t(14;19)] chromosomal translocation.

In one embodiment, the oncogene is bcl-6, the Ig locus is an IgH locus, and the cancer is diffuse large cell lymphoma. For example, patients having or suspected of having diffuse large cell lymphoma may exhibit oncogene bcl-6 translocated with an IgH locus. In some instances, oncogene bcl-6 translocated with an IgH locus may be overexpressed in such patients. The expression level of oncogene bcl-6 translocated with an IgH locus may be detected in such patients using known methods of measuring or detecting gene expression. Those patients having or suspected of having diffuse large cell lymphoma in which oncogene bcl-6 translocated with an IgH locus is overexpressed may benefit from administration of an effective amount of a bromodomain protein inhibitor in accordance with the methods disclosed herein. In an embodiment, the bcl-6 oncogene translocation is a [t(3;14)] chromosomal translocation.

In one embodiment, the oncogene is bcl-9, the Ig locus is an IgH locus, and the cancer is acute lymphoblastic lymphoma. For example, patients having or suspected of having acute lymphoblastic lymphoma may exhibit oncogene bcl-9 translocated with an IgH locus. In some instances, oncogene bcl-9 translocated with an IgH locus may be overexpressed in such patients. The expression level of oncogene bcl-9 translocated with an IgH locus may be detected in such patients using known methods of measuring or detecting gene expression. Those patients having or suspected of having acute lymphoblastic lymphoma in which oncogene bcl-9 translocated with an IgH locus is overexpressed may benefit from administration of an effective amount of a bromodomain protein inhibitor in accordance with the methods disclosed herein.

In one embodiment, the oncogene is bcl-10 and the cancer is mucosa-associated lymphatic tissue (MALT)-type lymphoma. For example, patients having or suspected of having mucosa-associated lymphatic tissue (MALT)-type lymphoma may exhibit oncogene bcl-10 translocated with an IgH locus. In some instances, oncogene bcl-10 translocated with an IgH locus may be overexpressed in such patients. The expression level of oncogene bcl-10 translocated with an IgH locus may be detected in such patients using known methods of measuring or detecting gene expression. Those patients having or suspected of having mucosa-associated lymphatic tissue (MALT)-type lymphoma in which oncogene bcl-10 translocated with an IgH locus is overexpressed may benefit from administration of an effective amount of a bromodomain protein inhibitor in accordance with the methods disclosed herein.

In one embodiment, the oncogene is c-maf, the Ig locus is an IgH locus, and the cancer is multiple myeloma. For example, patients having or suspected of having multiple myeloma may exhibit oncogene c-maf translocated with an IgH locus. In some instances, oncogene c-maf translocated with an IgH locus may be overexpressed in such patients. The expression level of oncogene c-maf translocated with an IgH locus may be detected in such patients using known methods of measuring or detecting gene expression. Those patients having or suspected of having multiple myeloma in which oncogene c-maf translocated with an IgH locus is overexpressed may benefit from administration of an effective amount of a bromodomain protein inhibitor in accordance with the methods disclosed herein. In an embodiment, the c-maf oncogene translocation is a [t(14;16)] chromosomal translocation.

In one embodiment, the oncogene is c-myc, the Ig locus is an IgH locus, and the cancer is Burkitt's lymphoma. For example, patients having or suspected of having Burkitt's lymphoma may exhibit oncogene c-myc translocated with an IgH locus. In some instances, oncogene c-myc translocated with an IgH locus may be overexpressed in such patients. The expression level of oncogene c-myc translocated with an IgH locus may be detected in such patients using known methods of measuring or detecting gene expression. Those patients having or suspected of having Burkitt's lymphoma in which oncogene c-myc translocated with an IgH locus is overexpressed may benefit from administration of an effective amount of a bromodomain protein inhibitor in accordance with the methods disclosed herein. In one embodiment, the c-myc oncogene translocation is a [t(14;16)] chromosomal translocation. In one embodiment, the c-myc oncogene translocation is a [t(8;22)] chromosomal translocation. In one embodiment, the c-myc oncogene translocation is a [t(2;8)] chromosomal translocation.

In one embodiment, the oncogene is c-myc, the Ig locus is an IgH locus, and the cancer is multiple myeloma. For example, patients having or suspected of having multiple myeloma may exhibit oncogene c-myc translocated with an IgH locus. In some instances, oncogene c-myc translocated with an IgH locus may be overexpressed in such patients. The expression level of oncogene c-myc translocated with an IgH locus may be detected in such patients using known methods of measuring or detecting gene expression. Those patients having or suspected of having multiple myeloma in which oncogene c-myc translocated with an IgH locus is overexpressed may benefit from administration of an effective amount of a bromodomain protein inhibitor in accordance with the methods disclosed herein.

In one embodiment, the oncogene is FGFR3, the Ig locus is an IgH locus, and the cancer is multiple myeloma. For example, patients having or suspected of having multiple myeloma may exhibit oncogene FGFR3 translocated with an IgH locus. In some instances, oncogene FGFR3 translocated with an IgH locus may be overexpressed in such patients. The expression level of oncogene FGFR3 translocated with an IgH locus may be detected in such patients using known methods of measuring or detecting gene expression. Those patients having or suspected of having multiple myeloma in which oncogene FGFR3 translocated with an IgH locus is overexpressed may benefit from administration of an effective amount of a bromodomain protein inhibitor in accordance with the methods disclosed herein. In one embodiment, the FGFR3 oncogene translocation is a [44;14)] chromosomal translocation.

In one embodiment, the oncogene is Lyt-10, the Ig locus is an IgH locus, and the cancer is diffuse large cell lymphoma. For example, patients having or suspected of having diffuse large cell lymphoma may exhibit oncogene Lyt-10 translocated with an IgH locus. In some instances, oncogene Lyt-10 translocated with an IgH locus may be overexpressed in such patients. The expression level of oncogene Lyt-10 translocated with an IgH locus may be detected in such patients using known methods of measuring or detecting gene expression. Those patients having or suspected of having diffuse large cell lymphoma in which oncogene Lyt-10 translocated with an IgH locus is overexpressed may benefit from administration of an effective amount of bromodomain protein inhibitor in accordance with the methods disclosed herein. In an embodiment, the Lyt-10 oncogene translocation is a [410;14)] chromosomal translocation.

In one embodiment, the oncogene is MUC1, the Ig locus is an IgH locus, and the cancer is extranodal lymphoma. For example, patients having or suspected of having extranodal lymphoma may exhibit oncogene MUC1 translocated with an IgH locus. In some instances, oncogene MUC1 translocated with an IgH locus may be overexpressed in such patients. The expression level of oncogene MUC1 translocated with an IgH locus may be detected in such patients using known methods of measuring or detecting gene expression. Those patients having or suspected of having extranodal lymphoma in which oncogene MUC1 translocated with an IgH locus is overexpressed may benefit from administration of an effective amount of a bromodomain protein inhibitor in accordance with the methods disclosed herein. In an embodiment, the MUC1 oncogene translocation is a [t(1;14)] chromosomal translocation.

In one embodiment, the oncogene is MUM1/IRF4, the Ig locus is an IgH locus, and the cancer is multiple myeloma. For example, patients having or suspected of having multiple myeloma may exhibit oncogene MUM1/IRF4 translocated with an IgH locus. In some instances, oncogene MUM1/IRF4 translocated with an IgH locus may be overexpressed in such patients. The expression level of oncogene MUM1/IRF4 translocated with an IgH locus may be detected in such patients using known methods of measuring or detecting gene expression. Those patients having or suspected of having multiple myeloma in which oncogene MUM1/IRF4 translocated with IgH locus is overexpressed may benefit from administration of an effective amount of a bromodomain protein inhibitor in accordance with the methods disclosed herein. In an embodiment, the MUM1/IRF4 oncogene translocation is a [t(6;14)] chromosomal translocation.

In one embodiment, the oncogene is Pax-5, the Ig locus is an IgH locus, and the cancer is lymphoplasmacytoid lymphoma. For example, patients having or suspected of having lymphoplasmacytoid lymphoma may exhibit oncogene Pax-5 translocated with an IgH locus. In some instances, oncogene Pax-5 translocated with an IgH locus may be overexpressed in such patients. The expression level of oncogene Pax-5 translocated with an IgH locus may be detected in such patients using known methods of measuring or detecting gene expression. Those patients having or suspected of having lymphoplasmacytoid lymphoma in which oncogene Pax-5 translocated with IgH locus is overexpressed may benefit from administration of an effective amount of a bromodomain protein inhibitor in accordance with the methods disclosed herein. In an embodiment, the Pax-5 oncogene translocation is a [t(9;14)] chromosomal translocation.

In one embodiment, the oncogene is Bcl6, the Ig locus is an IgL locus, and the cancer is a B-cell non-Hodgkin lymphoma (e.g., diffuse large cell lymphoma, adult aggressive lymphoma, etc). For example, patients having or suspected of having a B-cell non-Hodgkin lymphoma may exhibit oncogene Bcl6 translocated with an IgL locus. In some instances, oncogene Bcl6 translocated with an IgL locus may be overexpressed in such patients. The expression level of oncogene Bcl6 translocated with an IgL locus may be detected in such patients using known methods of measuring or detecting gene expression. Those patients having or suspected of having a B-cell non-Hodgkin lymphoma in which oncogene Bcl6 translocated with an IgL locus is overexpressed may benefit from administration of an effective amount of a bromodomain protein inhibitor in accordance with the methods disclosed herein. In an embodiment, the Bcl6 oncogene translocation is a [t(3;22)(q27;q11)] chromosomal translocation.

In one embodiment, the oncogene is c-Myc, the Ig locus is an IgL locus, and the cancer is a B-cell lymphoblastic leukemia and/or non-Hodgkin lymphomas (e.g., diffuse large cell lymphoma, adult aggressive lymphoma, Burkitt's lymphoma, etc). For example, patients having or suspected of having a B-cell lymphoblastic leukemia and/or a non-Hodgkin lymphoma may exhibit oncogene c-Myc translocated with an IgL locus. In some instances, oncogene c-Myc translocated with an IgL locus may be overexpressed in such patients. The expression level of oncogene c-Myc translocated with an IgL locus may be detected in such patients using known methods of measuring or detecting gene expression. Those patients having or suspected of having B-cell lymphoblastic leukemia and/or non-Hodgkin lymphomas in which oncogene c-Myc translocated with an IgL locus is overexpressed may benefit from administration of a bromodomain protein inhibitor in accordance with the methods disclosed herein. In an embodiment, the c-Myc oncogene translocation is a [t(8:22)(q24;q11)] chromosomal translocation.

The present invention contemplates that the bromodomain protein inhibitor can be an inhibitor of a BET bromodomain protein. In some embodiments, the bromodomain inhibitor is an inhibitor of Brd4 protein. In some embodiments, the bromodomain inhibitor is an inhibitor of Brd2 protein. In some embodiments, the bromodomain inhibitor is an inhibitor of Brd3 protein. In an embodiment, the bromodomain inhibitor is an inhibitor of BrdT protein.

It should be appreciated by those skilled in the art that the bromodomain protein inhibitors contemplated by the present invention can be any type of inhibitor. Examples of suitable inhibitors known to those skilled in the art include an antisense oligonucleotide, an aptamer, an intrabody, an oligopeptide, a ribozyme, an siRNA, a shRNA, and a small molecule inhibitor of bromodomain proteins.

In one embodiment, the bromodomain protein inhibitor of the present invention is a small molecule known as JQ1. JQ1 has selectivity within the BET family of bromodomain proteins, and may have selectivity beyond the family as well. Examples of bromodomains in which JQ1 may effectively inhibit include Brd2 (N-terminal), Brd2 (C-terminal), Brd3 (N-terminal), Brd3 (C-terminal), Brd4 (N-terminal), Brd4 (C-terminal), and CREBBP. JQ1 is [(S)-4-(4-Chlorophenyl)-2,3,9-trimethyl-6H-1-thia-5,7,8,9a-tetraaza-cyclopenta[e]azulen-6-yl]-acetic acid tert-butyl ester. JQ1 has the structure depicted in Formula I below:

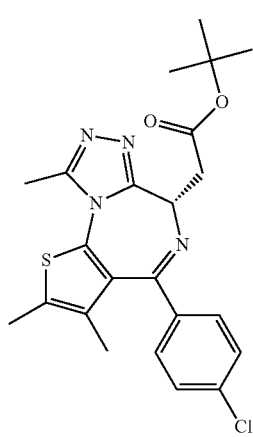

(I)

In certain embodiments, the inhibitors of the present invention may be administered as part of a pharmaceutical composition comprising the bromodomain protein inhibitor alone, the bromodomain inhibitor in combination with a cancer therapeutic agent, the bromodomain protein inhibitor conjugated to a cancer therapeutic agent, and/or the bromodomain protein inhibitor component linked to a delivery vehicle, which are each suitable for downregulating the expression of an oncogene translocated with an Ig locus, inhibiting the interaction between a bromodomain protein and an Ig regulatory element, and/or treating a cancer in which expression of an oncogene translocated with an Ig locus is increased (e.g., a hematological malignancy). Therapeutic formulations comprising the bromodomain proteins can be prepared for storage according to methods known to those skilled in the art. (REMINGTON'S PHARMACEUTICAL SCIENCES (A. Osol ed. 1980), which is hereby incorporated by reference in its entirety). In some embodiments, the bromodomain inhibitor is administered with a pharmaceutically acceptable carrier.

The active therapeutic ingredients of the pharmaceutical compositions (i.e. bromodomain inhibitors alone or linked to a cancer therapeutic agent) can be entrapped in microcapsules prepared using coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in REMINGTON'S PHARMACEUTICAL SCIENCES (A. Osol ed. 1980), which is hereby incorporated by reference in its entirety. In some embodiments, the bromodomain inhibitors of the present invention can be conjugated to the microcapsule delivery vehicle to target the delivery of the therapeutic agent to the site of the tumor. Sustained-release preparations may be prepared according to well known methods.

In another embodiment, the therapeutic treatment methods of the present invention involve the combined administration of one or more bromodomain inhibitors, in combination with a cancer therapeutic agent, or conjugated to a distinct chemotherapeutic agent, radiotherapeutic agent, or immunotherapeutic agent, resulting in the administration of a cocktail of chemotherapeutic, radiotherapeutic, and/or immunotherapeutic agents. In yet another embodiment, the bromodomain inhibitors alone or conjugated to the cancer therapeutic can be administered with one or more additional chemotherapeutic agents. Preparation and dosing schedules for such chemotherapeutic agents may be used according to manufacturers' instructions or as determined empirically by the skilled practitioner. Preparation and dosing schedules for such chemotherapy are also described in CHEMOTHERAPY SERVICE (M. C. Perry ed., 1992), which is hereby incorporated by reference in its entirety.

In an embodiment, the present invention contemplates the use of a bromodomain inhibitor for the treatment of a cancer characterized by overexpression of an oncogene translocated with an Ig locus.

In an embodiment, the present invention contemplates the use of a bromodomain inhibitor for the treatment of a cancer characterized by overexpression of an oncogene translocated with an Ig locus, with the proviso that said oncogene is not c-Myc.

In an embodiment, the present invention contemplates the use of a bromodomain inhibitor for the treatment of a cancer characterized by overexpression of an oncogene translocated with an Ig locus, with the proviso that said cancer is not AML.

In another aspect, the present invention includes a method for identifying an agent that interferes with binding of a bromodomain protein to an Ig regulatory element, such method comprising: (a) contacting a suitably conditioned cell containing a target gene under control of one or more Ig regulatory elements and a bromodomain protein which binds to said one or more Ig regulatory elements and activates expression of said target gene with a candidate agent; and (b) detecting expression of said target gene, wherein decreased expression of said target gene in the presence of said candidate agent as compared with expression of said target gene in the absence of said candidate agent is indicative of said agent's ability to interfere with binding of said bromodomain protein to said Ig regulatory element. In some embodiments, the method of identifying an agent that interferes with the binding of a bromodomain protein to an Ig regulatory element further comprises contacting said bromodomain protein immobilized onto a solid support with said candidate agent and a known inhibitor of said bromodomain protein, wherein said candidate agent's ability to outcompete said known inhibitor for binding to said bromodomain protein is indicative of said candidate agent's ability to interfere with binding of said bromodomain protein to said Ig regulatory element. Competitive binding assays and method of immobilizing a substrate to a solid support are routine methods known to those skilled in the art and any such methods now known, or later developed, can be used to assess the ability of the candidate agent to outcompete a known inhibitor of bromodomain protein for binding to the bromodomain. In some embodiments, the method of identifying an agent that interferes with the binding of a bromodomain protein to an Ig regulatory element further comprises comparing a level of bromodomain protein occupancy at said Ig regulatory element in the presence of said candidate agent to a control, wherein decreased bromodomain protein occupancy at said Ig regulatory element in the presence of said candidate agent as compared to in the absence of said candidate agent is indicative of bromodomain inhibitor activity of said candidate agent. In some embodiments, the control is the bromodomain protein occupancy at an Ig regulatory element in the presence of a known bromodomain inhibitor (e.g., JQ1). Those skilled in the art will appreciate, however, that any known bromodomain inhibitor can be used, including bromodomain inhibitors discovered according to the methods described herein.

In one embodiment, the method of identifying an agent that interferes with the binding of a bromodomain protein to an Ig regulatory element further comprises (c) contacting said bromodomain protein immobilized onto a solid support with said candidate agent and a known inhibitor of said bromodomain protein, wherein said candidate agent's ability to outcompete said known inhibitor for binding to said bromodomain protein is indicative of said candidate agent's ability to interfere with binding of said bromodomain protein to said Ig regulatory element; and (d) comparing a level of bromodomain protein occupancy at said Ig regulatory element in the presence of said candidate agent which is able to outcompete said known inhibitor to a control, wherein decreased bromodomain protein occupancy at said Ig regulatory element in the presence of said candidate agent as compared to in the absence of said candidate agent is indicative of bromodomain inhibitor activity of said candidate agent.

In certain embodiments, the candidate agent interferes with acetyl-lysine recognition by a central hydrophobic cavity of said bromodomain protein or interferes with acetyl-lysine anchoring by a hydrogen bond of an asparagine residue of said bromodomain protein.

In some embodiments, the agent or candidate agent is selected from the group consisting of an antisense oligonucleotide, an aptamer, an intrabody, an oligopeptide, a ribozyme, an siRNA, a shRNA, and a small molecule.

In an embodiment, the Ig regulatory element is an IgH regulatory element.

In some embodiments, the target gene is a reporter gene (e.g., a gene that encodes for a product that is readily quantifiable, e.g., GFP, etc.). In such instances, expression of the reporter gene can be detected by routine methods known to those skilled in the art to determine whether the candidate agent decreases expression of the reporter gene. In such instances, decreased expression of the reporter gene is indicative that the candidate agent interfered with binding to the Ig regulatory element, and that the candidate agent may be a lead candidate agent for additional screening.

In some embodiments, the target gene is fused to a protein tag. It should be appreciated by those skilled in the art that the protein tag may be used for a variety of purposes toward the characterization the target gene and its expression, including purification (e.g., affinity tag (GST)), separation (e.g., chromatography tag (FLAG-tag), visualization (e.g., fluorescence tag (GFP), subsequent analysis (e.g., epitope tags (HA-tag).

In some embodiments, the protein tag is selected from the group consisting of a fluorescent peptide and a poly His tag.

In an embodiment, target gene is an oncogene which is translocated with an Ig locus. In such instance, the target gene may be fused to another target gene as described above for measurement of expression of the target gene. In one embodiment, the oncogene is not c-Myc.

In one embodiment, the bromodomain protein is Brd4, the oncogene is c-Myc, and the Ig regulatory element is an IgH enhancer. In such embodiment, a method for identifying an agent that interferes with binding of a Brd4 to an IgH regulatory element comprises: (a) contacting a suitably conditioned cell containing a target gene under control of one or more IgH regulatory elements (e.g., an IgH enhancer or sequence adjacent to an enhancer) and a Brd4 protein which binds to said one or more IgH regulatory elements and activates expression of said target gene with a candidate agent; and (b) detecting expression of said target gene, wherein decreased expression of said target gene in the presence of said candidate agent as compared with expression of said target gene in the absence of said candidate agent is indicative of said agent's ability to interfere with binding of said Brd4 protein to said IgH regulatory element. The candidate agents identified by performing steps (a) and (b) can optionally be further screened for their ability to interfere with binding of Brd4 to an IgH regulatory element by performing step (c) contacting the bromodomain protein (e.g., Brd4) immobilized onto a solid support with said candidate agent and a known inhibitor of said bromodomain protein (e.g., JQ1), wherein said candidate agent's ability to outcompete said known inhibitor for binding to said bromodomain protein is indicative of said candidate agent's ability to interfere with binding of said bromodomain protein to said Ig regulatory element. The candidate agents identified by performing the screen described in step (c) can further be screened for its ability to interfere with binding of the bromodomain protein and the Ig regulatory element by performing the step of (d) comparing a level of bromodomain protein (e.g., Brd 4) occupancy at said Ig regulatory element in the presence of said candidate agent which is able to outcompete said known inhibitor (e.g., JQ1) to a control, wherein decreased bromodomain protein occupancy at said Ig regulatory element (e.g., an IgH enhancer) in the presence of said candidate agent as compared to in the absence of said candidate agent is indicative of bromodomain inhibitor activity of said candidate agent.

In another aspect, a method for identifying an inhibitor of a bromodomain protein is disclosed, such method comprising: (a) contacting a cell line expressing an oncogene translocated with an Ig locus with a candidate agent; (b) measuring the level of bromodomain protein occupancy at a regulatory element of said Ig locus; and (c) comparing said level of bromodomain occupancy at said regulatory element of said Ig locus to a control, wherein decreased bromodomain protein occupancy at said regulatory element of said Ig locus in the presence of the candidate agent as compared to in the absence of said candidate agent is indicative of bromodomain inhibitory activity of said candidate agent. Those skilled in the art will appreciate that an exemplary method of performing such method for identifying an inhibitor of bromodomain protein is described in further detail in Example 1 below.

Generally, any control which is able to assess the ability of a bromodomain inhibitor to interfere with binding of a bromodomain protein to an Ig regulatory element can be employed in accordance with the methods disclosed herein. In certain embodiments, the control is a control bromodomain occupancy level or reference or standard level of bromodomain protein occupancy at an Ig regulatory element. In some embodiments, the control bromodomain occupancy level is determined by contacting said cell line with a known bromodomain protein inhibitor, and measuring a level of bromodomain occupancy at said regulatory element of said Ig locus.

In certain embodiments, the methods for identifying a bromodomain inhibitor contemplate employing a known bromodomain protein inhibitor as a control or for a functional comparator. In an embodiment, the known bromodomain protein inhibitor is small molecule JQ1.

It should be appreciated that any oncogene which is capable of translocation with an Ig locus can be the subject of the identification methods of the present invention. In an embodiment, the oncogene is c-myc.

The present invention contemplates that any cell line which is suitable for expressing an oncogene translocated with an Ig locus can be used in accordance with the methods disclosed herein. In an embodiment, the cell line is a multiple myeloma cell line.

Generally, the Ig regulatory element can be any regulatory element or sequence associated with an Ig locus which contributes to the expression of an oncogene translocated with the Ig locus. The skilled artisan will also recognize that the Ig regulatory element can comprise a binding site that is located at any location within the broader Ig regulatory region. In certain embodiments, the Ig regulatory element is an IgH enhancer. In some embodiments, the IgH enhancer is selected from the group consisting of E1, E2, E3, and E4. IgH enhancers E1, E2, E3, and E4 are described in further detail in Example 1 below. In other embodiments, the Ig regulatory element is a regulatory element located within a region or adjacent to a region in which the IgH enhancer is located. In an embodiment, the Ig regulatory element is a regulatory element which shares sequence similarity or sequence complementarily to an IgH enhancer. In an embodiment, the regulatory element comprises a sequence that spans approximately 100 bp along an Ig regulatory region.

Those skilled in the art will appreciate that a variety of known and routine methods can be used to measure the level of bromodomain protein occupancy at a regulatory element of an Ig locus. In some embodiments, said step of measuring said level of bromodomain protein occupancy at said regulatory element of said Ig locus is performed using bromodomain protein ChIP-PCR analysis. In such embodiments, said ChIP-PCR analysis is performed using oligonucleotide primers complementary to at least a portion of a sequence of said regulatory element. In certain embodiments, said step of measuring said level of bromodomain protein occupancy at said regulatory element of said Ig locus is performed using sequencing techniques. In certain embodiments, said step of measuring said level of bromodomain protein occupancy at said regulatory element of said Ig locus is performed using a microarray.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1: Bromodomain Proteins Bind Ig Enhancers, Regulating Translocated Oncogene Expression and Function Background and Introduction c-Myc overexpression in cancer uncouples growth-factor stimulation and cell proliferation. c-Myc can be overexpressed through multiple mechanisms in tumor cells, including gene amplification, chromosomal translocation and single nucleotide polymorphisms (SNP). The most common mechanism is through MYC gene amplifications. This was first identified in the HL-60 human premyelocytic leukemia cell line, which contains 10 to 20 copies of the MYC gene [4, 5]. Some cancers can contain upwards of 150 copies of the MYC gene [6]. Chromosomal translocations occur in hematological malignancies, including Burkitt's lymphoma [7, 8]. The translocations typically occur between MYC and the immunoglobulin heavy chain (IgH) locus and MYC expression is then controlled by IgH regulatory elements [7-9]. Because IgH is highly expressed in B- and T-cells, this leads to massive overexpression of MYC and uncontrolled proliferation. Additionally, high-risk cancer SNPs associated with colorectal, breast, bladder, ovarian and prostate cancer at 8q24 have been mapped to MYC enhancer elements [10-14]. These regions form chromosome loops with the MYC promoter region to regulate its expression. These SNPs may influence MYC expression by altering the affinity of transcription factors like Tcf4, a terminal component of the Wnt/b-catenin signaling pathway, for binding sites in the enhancer region [14]. Because of c-Myc's role in promoting proliferation, overexpression of this transcription factor contributes to a key aspect of cancer: unregulated proliferation.

Nevertheless, since the historic discovery of MYC as a human oncogene more than thirty years ago, a therapeutic approach to modulating c-Myc transcription has remained elusive. The absence of a clear ligand-binding domain establishes a formidable obstacle toward directly inhibiting c-Myc function, a challenging feature of many compelling transcription factor targets in cancer [22]. High-resolution structures of the c-Myc/Max complex fail to identify a hydrophobic involution compatible with the positioning of an organic small molecule [23].

We therefore have undertaken to target c-Myc transcriptional function by another means, namely the disruption of chromatin-dependent signal transduction. c-Myc transcription is associated locally and globally with increases in histone lysine side-chain acetylation [24-26], a covalent modification of chromatin regionally associated with transcriptional activation [27, 28]. Histone acetylation templates the assembly of higher-ordered transcriptional complexes by the recruitment of proteins possessing one or more acetyl-lysine binding modules or bromodomains [29, 30]. Members of the bromodomain and extra-terminal (BET) subfamily of human bromodomains (Brd2, Brd3, Brd4 and Brdt) associate with acetylated chromatin and facilitate transcriptional activation by increasing the effective molarity of recruited transcriptional activators. Notably, Brd4 has been shown to mark select M/G1 genes in mitotic chromatin as transcriptional memory and direct post-mitotic transcription [31], notably via direct interaction with the positive transcription elongation factor complex b (P-TEFb) [32]. The discovery that c-Myc regulates promoter-proximal pause release of Pol II, also through the recruitment of P-TEFb [33], established a rationale for targeting BET bromodomains to inhibit c-Myc dependent transcription.

Recently, the development and biochemical characterization of a first potent, selective small-molecule inhibitor of BET bromodomains, JQ1, was reported[34]. JQ1 is a thieno-triazolo-1,4-diazepine which displaces BET bromodomains from nuclear chromatin by competitively binding to the acetyl-lysine recognition pocket. In the present study, we leverage the biochemical and pharmacologic properties of JQ1 as a chemical probe [35], to interrogate the role of BET bromodomains in Myc-dependent transcription and to explore the putative role of BET bromodomains as cancer dependencies.

Multiple myeloma (MM) represents an ideal model system for these mechanistic and translational questions given the known role of MYC in disease pathophysiology. MM is an incurable hematologic malignancy, typified by the accumulation of malignant plasma cells harboring diverse genetic lesions [36]. Rearrangement or translocation of MYC is among the most common somatic events in early and late stage MM [37-42], and transcriptional profiling identifies Myc pathway activation in more than 60% of patient-derived MM cells [43]. Experimental support for the central role of c-Myc in the pathogenesis of MM is contributed by an informative, genetically-engineered murine model of MM. Lineage-specific and stochastic Activation-Induced Deaminase (AID)-dependent activation of a conditional MYC transgene in the late stages of B-cell differentiation establishes genetically-engineered mice with a plasma cell malignancy that shares clinically relevant features of MM [41]. Thus, MYC dysregulation represents a largely unifying molecular feature observed across the otherwise complex genetic pathophysiology of MM, from the pre-malignant monoclonal gammopathy of undetermined significance (MGUS) to the advanced stage of plasma cell leukemia (PCL).

Results and Discussion

To test BET bromodomain inhibitors as a strategy to downregulate the cMyc transcriptional network and the mechanism of downregulation, multiple myeloma cells were treated with JQ1. Treatment with JQ1 induced a potent antiproliferative effect, consistent with loss of cMyc function. Furthermore, JQ1 treatment caused rapid downregulation of cMyc protein levels and a genome-wide downregulation of cMyc target genes.

MYC translocation with IGH (8;14) is a common form of deregulation in multiple myeloma. We reasoned that early and sustained JQ1-induced suppression of MYC transcription may be mechanistically explained by physical interaction of BRD4 with regulatory elements influencing MYC expression. Indeed, avid binding of BRD4 to established IgH enhancers was observed by chromatin immunoprecipitation (ChIP) in MM.1S cells (FIGS. 1A, 1B), which harbor an IgH insertion proximal to the MYC transcriptional start site (TSS). BRD4 binding was not observed at five characterized enhancer regions adjacent to the MYC gene [13]. JQ1 treatment (500 nM) for 24 hours significantly depleted BRD4 binding to IgH enhancers and the TSS, supporting direct regulation of MYC transcription by BET bromodomains, and a model whereby BRD4 acts as a co-activator of MYC transcription potentially through long-range interactions with distal enhancer elements. This implicates Brd4 as a positive regulator of translocated IGH-MYC expression and a target for downregulating MYC in these cells.

Our results show that BET domain inhibition is a viable strategy to downregulate the cMyc transcriptional network in multiple myeloma and potentially in other blood cancers driven by translocated IGH-MYC. Additionally, because Brd4 binds at the IGH regulatory elements and JQ1 treatment competes it off these sites, BET bromodomain inhibition could be used to downregulate other oncogenes overexpressed through immunoglobulin translocations.

The foregoing results establish the use of bromodomain inhibitors (e.g., BET bromodomain inhibitors) as an effective strategy to downregulate oncogenes overexpressed through translocation with the Ig (e.g., IgH) regulatory elements. The foregoing results provide evidence that bromodomain inhibitor treatment works for IGH-cMyc translocations in multiple myeloma because the target of JQ1 (Brd4) binds these regulatory elements and treatment with JQ1 competes this protein off chromatin. The IGH-MYC translocation occurs in a number of other blood cancers, including Burkitt's Lymphoma, for example. Translocation between oncogenes and IGH is a common occurrence in many B cell malignancies. Translocations involving IGH with other oncogenes are also found, including the onco-genes Bcl2, Ccnd1 [44], c-Maf, Pax5, Pim1 [45], Bcl6, Irf4 [46], Il3, Lyt10, Bcl3 and Malt1 [47][48, 49].

Experimental Procedures Used in the Examples

Approximately $1 \times 10^8$ MM1S cells were treated with 500 nM JQ1 or DMSO for 24 hours and crosslinked with 1.1% formaldehyde (10× crosslink solution contains 11% formaldehyde, 50 mM Hepes pH7.3, 100 mM NaCl, 1 mM EDTA p118.0, 0.5 mM EGTA pH8.0) to the growth media followed by two washes with PBS. Cells were scraped and frozen in liquid nitrogen. Brd4 ChIP-PCR analysis was done on these cells following the protocol in Rahl et al. Cell 2010. In brief, 75 ul of Dynal magnetic beads (Sigma) were blocked with 0.5% BSA (w/v) in PBS. Magnetic beads were bound with 6.25 ug of Brd4 antibody (Bethyl Labs, A310-985A, lot A301-985A-1, FIG. 1A or Sigma, HPA015055-100, lot A31530, FIG. 1B). Crosslinked cells were lysed with lysis buffer 1 (50 mM Hepes pH7.3, 140 mM NaCl, 1 mM EDTA, 10% glycerol, 0.5% NP-40, and 0.25% Triton X-100) and washed with lysis buffer 2 (10 mM Tris-HCl pH8.0, 200 mM NaCl, 1 mM EDTA pH8.0 and 0.5 mM EGTA pH8.0). Cells were resuspended and sonicated in lysis buffer 3 (50 mM Tris-HCl pH7.5, 140 mM NaCl, 1 mM EDTA, 1 mM EGTA, 1% Triton X-100, 0.1% Na-deoxycholate, 0.1% SDS) for 10 cycles at 30 seconds each on ice (18 watts) with 60 seconds on ice between cycles. Sonicated lysates were cleared and incubated overnight at 4° C. with magnetic beads bound with antibody to enrich for DNA fragments bound by the indicated factor. Beads were washed three times with sonication buffer, one time with sonication buffer with 500 mM NaCl, one time with LiCl wash buffer (20 mM Tris pH8.0, 1 mM EDTA, 250 mM LiCl, 0.5% NP-40, 0.5% Na-deoxycholate) and one time with TE. DNA was eluted in elution buffer. Cross-links were reversed overnight. RNA and protein were digested using RNAse A and Proteinase K, respectively and DNA was purified with phenol chloroform extraction and ethanol precipitation.

Brd4 ChIP and input DNA were analyzed using SYBR Green real-time PCR analysis (Applied Biosystems). ENCODE H3K27Ac ChIP-seq data available on the UCSC genome browser (available on the World Wide Web at subdomain genome.ucsc.edu/ENCODE/) was used to identify potential tissue-specific MYC enhancer and IGH enhancer regulatory elements and oligos were designed for these regions. Fold enrichment was determined from triplicate PCR reactions at five potential enhancer regions adjacent to the MYC gene in non-translocated cells (MYC_E1, MYC_E2, MYC_E3, MYC_E4, MYC_E5), the MYC transcriptional start site (MYC_TS1, MYC_TS2), IGH enhancer regions (IGH_E1, IGH_E2, IGH_E3, IGH_E4), and two negative regions upstream of the MYC enhancers (MYC_NR2, MYC_NR3) over input DNA using DDCt over the negative region MYC_NR1. The oligos used for this analysis are:

| Primer Set | HG19 Region Location | F/R | Sequence | SEQ ID NO |
|---|---|---|---|---|
| MYC_NR1 | chr8: 127,714,271-127,788,621 | FWD<br>REV | GCAGCTAGATCGTTGGGAAG<br>GCTGGTGATTTCAGTGCAGA | SEQ ID NO: 1<br>SEQ ID NO: 2 |
| MYC_NR2 | chr8: 127,714,271-127,788,621 | FWD<br>REV | TCCTGGGTAGGAACCAGTTG<br>ACTCACCAAGAGCTCCTCCA | SEQ ID NO: 3<br>SEQ ID NO: 4 |
| MYC_NR3 | chr8: 127,714,271-127,788,621 | FWD<br>REV | AAGCCAACCCATCACTGAAC<br>TTCCCATGTTACCCACCACT | SEQ ID NO: 5<br>SEQ ID NO: 6 |
| MYC_E1 | chr8: 127,845,547-127,846,357 | FWD<br>REV | TGCTAATTGTGCCTCTCCTGT<br>ACTCCCAGCAAATCAGCCTA | SEQ ID NO: 7<br>SEQ ID NO: 8 |
| MYC_E2 | chr8: 128,218,650-128,218,982 | FWD<br>REV | TTGTCTTCCTCATGCCTTCTC<br>AGCTGCAATTCAGGGTTACTG | SEQ ID NO: 9<br>SEQ ID NO: 10 |
| MYC_E3 | chr8: 128,237,690-128,237,903 | FWD<br>REV | TTTGGGCAGACACTGACTTG<br>AAGCAGAAACAGGACCCAGA | SEQ ID NO: 11<br>SEQ ID NO: 12 |
| MYC_E4 | chr8: 128,307,286-128,307,531 | FWD<br>REV | GAAATGTGAGGGCACATCGT<br>ATACCTGCTGGAGCATTTGG | SEQ ID NO: 13<br>SEQ ID NO: 14 |
| MYCE_5 | chr8: 128,568,909-128,569,272 | FWD<br>REV | TCAGCCTGTGGGCTCTAGTT<br>AGGGAAGTGCTACCCCATCT | SEQ ID NO: 15<br>SEQ ID NO: 16 |
| MYC_TS1 | chr8: 128,747,740-128,748,029 | FWD<br>REV | ACACTAACATCCCACGCTCTG<br>GATCAAGAGTCCCAGGGAGA | SEQ ID NO: 17<br>SEQ ID NO: 18 |
| MYC_TS2 | chr8: 128,749,029-128,749,395 | FWD<br>REV | GGTCGGACATTCCTGCTTTA<br>GATATGCGGTCCCTACTCCA | SEQ ID NO: 19<br>SEQ ID NO: 20 |
| IGH_E1 | chr14: 106,047,824-106,049,452 | FWD<br>REV | TGGGGTACAAGAGGCTTCAG<br>TACAGGAGTGGGGACAGGAA | SEQ ID NO: 21<br>SEQ ID NO: 22 |
| IGH_E2 | chr14: 106,047,824-106,049,452 | FWD<br>REV | GTTCTCTGGCTGGAACACCT<br>CCCCATCACCTGCAGAAATA | SEQ ID NO: 23<br>SEQ ID NO: 24 |
| IGH_E3 | chr14: 106,167,019-106,167,760 | FWD<br>REV | CCACAGGGCTATTTTGGGTA<br>GCCATGCCGTTTGTATTCTC | SEQ ID NO: 25<br>SEQ ID NO: 26 |
| IGH_E4 | chr14: 106,167,019-106,167,760 | FWD<br>REV | GGGAGGCCATGCTGTTTGTATTCT<br>AACAGCAGTTCTCTGGCTGGAACA | SEQ ID NO: 27<br>SEQ ID NO: 28 |

REFERENCES

1. Nesbit, C. E., J. M. Tersak, and E. V. Prochownik, *MYC oncogenes and human neoplastic disease.* Oncogene, 1999. 18(19): p. 3004-16.
2. Eilers, M. and R. N. Eisenman, *Myc's broad reach.* Genes Dev, 2008. 22(20): p. 2755-66.
3. Meyer, N. and L. Z. Penn, *Reflecting on 25 years with MYC.* Nat Rev Cancer, 2008. 8(12): p. 976-90.
4. Collins, S. and M. Groudine, *Amplification of endogenous myc-related DNA sequences in a human myeloid leukaemia cell line.* Nature, 1982. 298(5875): p. 679-81.
5. Dalla-Favera, R., F. Wong-Staal, and R. C. Gallo, *One gene amplification in promyelocytic leukaemia cell line HL-60 and primary leukaemic cells of the same patient.* Nature, 1982. 299(5878): p. 61-3.
6. Sauter, G., et al., *c-myc copy number gains in bladder cancer detected by fluorescence in situ hybridization.* Am J Pathol, 1995. 146(5): p. 1131-9.
7. Leder, P., et al., *Translocations among antibody genes in human cancer.* Science, 1983, 222(4625): p. 765-71.
8. Klein, G., *Specific chromosomal translocations and the genesis of B-cell-derived tumors in mice and men.* Cell, 1983. 32(2): p. 311-5.
9. Gostissa, M., et al., *Long-range oncogenic activation of Igh-c-myc translocations by the Igh 3' regulatory region.* Nature, 2009. 462(7274): p. 803-7.
10. Easton, D. F., et al., *Genome-wide association study identifies novel breast cancer susceptibility loci.* Nature, 2007. 447(7148): p. 1087-93.
11. Greenman, C., et al., *Patterns of somatic mutation in human cancer genomes.* Nature, 2007. 446(7132): p. 153-8.
12. Kiemeney, L. A., et al., *Sequence variant on 8q24 confers susceptibility to urinary bladder cancer.* Nat Genet, 2008. 40(11): p. 1307-12.
13. Pomerantz, M. M., et al., *The 8q24 cancer risk variant rs6983267 shows long-range interaction with MYC in colorectal cancer.* Nat Genet, 2009. 41(8): p. 882-4.
14. Wright, J. B., S. J. Brown, and M. D. Cole, *Upregulation of c-MYC in cis through a large chromatin loop linked to a cancer risk-associated single-nucleotide polymorphism in colorectal cancer cells.* Mol Cell Biol, 2010. 30(6): p. 1411-20.
15. Felsher, D. W. and J. M. Bishop, *Reversible tumorigenesis by MYC in hematopoietic lineages.* Mol Cell, 1999. 4(2): p. 199-207.
16. Flores, I., et al., *Defining the temporal requirements for Myc in the progression and maintenance of skin neoplasia.* Oncogene, 2004. 23(35): p. 5923-30.
17. Pelengaris, S., M. Khan, and G. I. Evan, *Suppression of Myc-induced apoptosis in beta cells exposes multiple oncogenic properties of Myc and triggers carcinogenic progression.* Cell, 2002. 109(3): p. 321-34.

18. Pelengaris, S., et al., *Reversible activation of c-Myc in skin: induction of a complex neoplastic phenotype by a single oncogenic lesion.* Mol Cell, 1999. 3(5): p. 565-77.
19. Jain, M., et al., *Sustained loss of a neoplastic phenotype by brief inactivation of MYC.* Science, 2002. 297(5578): p. 102-4.
20. Soucek, L., et al., *Modelling Myc inhibition as a cancer therapy.* Nature, 2008. 455(7213): p. 679-83.
21. Gamberi, G., et al., *C-myc and c-fos in human osteosarcoma: prognostic value of mRNA and protein expression.* Oncology, 1998. 55(6): p. 556-63.
22. Heidenreich, O., *Targeting oncogenes with siRNAs.* Methods Mol Biol, 2009. 487: p. 221-42.
23. Nair, S. K. and S. K. Burley, *X-ray structures of Myc-Max and Mad-Max recognizing DNA. Molecular bases of regulation by proto-oncogenic transcription factors.* Cell, 2003. 112(2): p. 193-205.
24. Martinato, F., et al., *Analysis of Myc-induced histone modifications on target chromatin.* PLoS One, 2008. 3(11): p. e3650.
25. Frank, S. R., et al., *MYC recruits the TIP60 histone acetyltransferase complex to chromatin.* EMBO Rep, 2003. 4(6): p. 575-80.
26. Vervoorts, J., et al., *Stimulation of c-MYC transcriptional activity and acetylation by recruitment of the cofactor CBP.* EMBO Rep, 2003. 4(5): p. 484-90.
27. Hebbes, T. R., A. W. Thorne, and C. Crane-Robinson, *A direct link between core histone acetylation and transcriptionally active chromatin.* Embo J, 1988. 7(5): p. 1395-402.
28. Turner, B. M., *Decoding the nucleosome.* Cell, 1993. 75(1): p. 5-8.
29. Hassan, A. H., et al., *Function and selectivity of bromodomains in anchoring chromatin-modifying complexes to promoter nucleosomes.* Cell, 2002. 111(3): p. 369-79.
30. Moriniere, J., et al., *Cooperative binding of two acetylation marks on a histone tail by a single bromodomain.* Nature, 2009. 461(7264): p. 664-8.
31. Dey, A., et al., *Brd4 marks select genes on mitotic chromatin and directs postmitotic transcription.* Mol Biol Cell, 2009. 20(23): p. 4899-909.
32. Bisgrove, D. A., et al., *Conserved P-TEFb-interacting domain of BRD4 inhibits HIV transcription.* Proc Natl Acad Sci USA, 2007. 104(34): p. 13690-5.
33. Rahl, P. B., et al., *c-Myc regulates transcriptional pause release.* Cell, 2010. 141(3): p. 432-45.
34. Filippakopoulos, P., et al., *Selective inhibition of BET bromodomains.* Nature, 2010. 468(7327): p. 1067-73.
35. Frye, S. V., *The art of the chemical probe.* Nat Chem Biol, 2011. 6(3): p. 159-161.
36. Chapman, M. A., et al., *Initial genome sequencing and analysis of multiple myeloma.* Nature, 2011. 471(7339): p. 467-72.
37. Sumegi, J., et al., *Amplification of the c-myc oncogene in human plasma-cell leukemia.* Int J Cancer, 1985. 36(3): p. 367-71.
38. Avet-Loiseau, H., et al., *Rearrangements of the c-myc oncogene are present in 15% of primary human multiple myeloma tumors.* Blood, 2001. 98(10): p. 3082-6.
39. Avet-Loiseau, H., et al., *Genetic abnormalities and survival in multiple myeloma: the experience of the Intergroupe Francophone du Myelome.* Blood, 2007. 109(8): p. 3489-95.
40. Kuehl, W. M., et al., *Dysregulation of c-myc in multiple myeloma.* Curr Top Microbiol Immunol, 1997. 224: p. 277-82.
41. Chesi, M., et al., *AID-dependent activation of a MYC transgene induces multiple myeloma in a conditional mouse model of post-germinal center malignancies.* Cancer Cell, 2008. 13(2): p. 167-80.
42. Kuehl, W. M. and P. L. Bergsagel, *Multiple myeloma: evolving genetic events and host interactions*, Nat Rev Cancer, 2002. 2(3): p. 175-87.
43. Chng, W. J., et al., *Clinical and biological implications of MYC activation: a common difference between MGUS and newly diagnosed multiple myeloma.* Leukemia, 2011. 25(6): p. 1026-35.
44. Gabrea, A., et al., *Insertion of excised IgH switch sequences causes overexpression of cyclin D1 in a myeloma tumor cell.* Mol Cell, 1999. 3(1): p. 119-23.
45. Pasqualucci, L., et al., *Hypermutation of multiple proto-oncogenes in B-cell diffuse large-cell lymphomas.* Nature, 2001. 412(6844): p. 341-6.
46. Salaverria, I., et al., *Translocations activating IRF4 identify a subtype of germinal center-derived B-cell lymphoma affecting predominantly children and young adults.* Blood, 2011. 118(1): p. 139-147.
47. Murga Penas, E. M., et al., *The t(14;18)(q32;q21)/IGH-MALT1 translocation in MALT lymphomas contains templated nucleotide insertions and a major breakpoint region similar to follicular and mantle cell lymphoma.* Blood, 2010. 115(11): p. 2214-9.
48. Kuppers, R. and R. Dalla-Favera, *Mechanisms of chromosomal translocations in B cell lymphomas.* Oncogene, 2001. 20(40): p. 5580-94.
49. Hideshima, T., et al., *Advances in biology of multiple myeloma: clinical applications.* Blood, 2004. 104(3): p. 607-18.

What is claimed is:

1. A method for identifying an agent that interferes with binding of a bromodomain protein 4 (Brd4) to an immunoglobulin heavy chain (IgH) regulatory element comprising:
  (a) contacting a cell containing a target gene under control of the IgH regulatory element and a Brd4 protein which binds to said IgH regulatory element and activates expression of said target gene with a candidate agent;
  (b) detecting expression of said target gene;
  (c) identifying a candidate agent that decreases expression of said target gene as compared with expression of said target gene in the absence of said candidate agent; and
  (d) further screening said identified candidate by: (i) contacting Brd4 protein immobilized on a solid support with said identified candidate agent and JQ1, wherein said identified candidate agent's ability to outcompete said JQ1 for binding to Brd4 is indicative of said identified candidate agent's ability to interfere with binding of said Brd4 protein to said IgH regulatory element and (ii) comparing a level of Brd4 protein occupancy at said IgH regulatory element in the presence of said identified candidate agent which is able to outcompete JQ1 to a control, wherein decreased Brd4 protein occupancy at said IgH regulatory element in the presence of said identified candidate agent which is able to outcompete JQ1 as compared to in the absence of said candidate agent which is able to outcompete JQ1 is indicative of bromodomain inhibitor activity.

2. The method of claim 1 wherein said candidate agent is selected from the group consisting of an antisense oligonucleotide, an aptamer, an intrabody, an oligopeptide, a ribozyme, an siRNA, a shRNA, and a small molecule.

3. The method of claim 1 wherein said target gene is an oncogene which is translocated with an IgH locus.

4. The method of claim 3 wherein said oncogene is not c-Myc.

5. The method of claim 3 wherein said oncogene is selected from the group consisting of Bcl2, Ccnd1, c-Maf, Pax5, Pim1, Bcl6, Irf4, Il3, Lyt10, Bcl3, and Malt1.

6. The method of claim 3 wherein said oncogene is c-Myc.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial
<220> FEATURE:
<223> OTHER INFORMATION: PCT oligonucleotide primer

<400> SEQUENCE: 1
gcagctagat cgttgggaag                                              20

<210> SEQ ID NO 2
<211> LENGTH: 20

```
<212> TYPE: DNA
<213> ORGANISM: Artificial
<220> FEATURE:
<223> OTHER INFORMATION: PCT oligonucleotide primer

<400> SEQUENCE: 2
gctggtgatt tcagtgcaga                                           20

<210> SEQ ID NO 3
<211> LENGTH: 20
<212> TYPE: DNA
<213> ORGANISM: Artificial
<220> FEATURE:
<223> OTHER INFORMATION: PCT oligonucleotide primer

<400> SEQUENCE: 3
tcctgggtag gaaccagttg                                           20

<210> SEQ ID NO 4
<211> LENGTH: 20
<212> TYPE: DNA
<213> ORGANISM: Artificial
<220> FEATURE:
<223> OTHER INFORMATION: PCT oligonucleotide primer

<400> SEQUENCE: 4
actcaccaag agctcctcca                                           20

<210> SEQ ID NO 5
<211> LENGTH: 20
<212> TYPE: DNA
<213> ORGANISM: Artificial
<220> FEATURE:
<223> OTHER INFORMATION: PCT oligonucleotide primer

<400> SEQUENCE: 5
aagccaaccc atcactgaac                                           20

<210> SEQ ID NO 6
<211> LENGTH: 20
<212> TYPE: DNA
<213> ORGANISM: Artificial
<220> FEATURE:
<223> OTHER INFORMATION: PCT oligonucleotide primer

<400> SEQUENCE: 6
ttcccatgtt acccaccact                                           20

<210> SEQ ID NO 7
<211> LENGTH: 21
<212> TYPE: DNA
<213> ORGANISM: Artificial
<220> FEATURE:
<223> OTHER INFORMATION: PCT oligonucleotide primer

<400> SEQUENCE: 7
tgctaattgt gcctctcctg t                                         21

<210> SEQ ID NO 8
<211> LENGTH: 20
<212> TYPE: DNA
<213> ORGANISM: Artificial
<220> FEATURE:
<223> OTHER INFORMATION: PCT oligonucleotide primer

<400> SEQUENCE: 8
```
actcccagca aatcagccta           20

<210> SEQ ID NO 9
<211> LENGTH: 21
<212> TYPE: DNA
<213> ORGANISM: Artificial
<220> FEATURE:
<223> OTHER INFORMATION: PCT oligonucleotide primer

<400> SEQUENCE: 9
ttgtcttcct catgccttct c         21

<210> SEQ ID NO 10
<211> LENGTH: 21
<212> TYPE: DNA
<213> ORGANISM: Artificial
<220> FEATURE:
<223> OTHER INFORMATION: PCT oligonucleotide primer

<400> SEQUENCE: 10
agctgcaatt cagggttact g         21

<210> SEQ ID NO 11
<211> LENGTH: 20
<212> TYPE: DNA
<213> ORGANISM: Artificial
<220> FEATURE:
<223> OTHER INFORMATION: PCT oligonucleotide primer

<400> SEQUENCE: 11
tttgggcaga cactgacttg           20

<210> SEQ ID NO 12
<211> LENGTH: 20
<212> TYPE: DNA
<213> ORGANISM: Artificial
<220> FEATURE:
<223> OTHER INFORMATION: PCT oligonucleotide primer

<400> SEQUENCE: 12
aagcagaaac aggacccaga           20

<210> SEQ ID NO 13
<211> LENGTH: 20
<212> TYPE: DNA
<213> ORGANISM: Artificial
<220> FEATURE:
<223> OTHER INFORMATION: PCT oligonucleotide primer

<400> SEQUENCE: 13
gaaatgtgag ggcacatcgt           20

<210> SEQ ID NO 14
<211> LENGTH: 20
<212> TYPE: DNA
<213> ORGANISM: Artificial
<220> FEATURE:
<223> OTHER INFORMATION: PCT oligonucleotide primer

<400> SEQUENCE: 14
atacctgctg gagcatttgg           20

<210> SEQ ID NO 15
<211> LENGTH: 20
<212> TYPE: DNA
<213> ORGANISM: Artificial

```
<220> FEATURE:
<223> OTHER INFORMATION: PCT oligonucleotide primer

<400> SEQUENCE: 15
tcagcctgtg ggctctagtt                                              20

<210> SEQ ID NO 16
<211> LENGTH: 20
<212> TYPE: DNA
<213> ORGANISM: Artificial
<220> FEATURE:
<223> OTHER INFORMATION: PCT oligonucleotide primer

<400> SEQUENCE: 16
agggaagtgc tacccccatct                                             20

<210> SEQ ID NO 17
<211> LENGTH: 21
<212> TYPE: DNA
<213> ORGANISM: Artificial
<220> FEATURE:
<223> OTHER INFORMATION: PCT oligonucleotide primer

<400> SEQUENCE: 17
acactaacat cccacgctct g                                            21

<210> SEQ ID NO 18
<211> LENGTH: 20
<212> TYPE: DNA
<213> ORGANISM: Artificial
<220> FEATURE:
<223> OTHER INFORMATION: PCT oligonucleotide primer

<400> SEQUENCE: 18
gatcaagagt cccagggaga                                              20

<210> SEQ ID NO 19
<211> LENGTH: 20
<212> TYPE: DNA
<213> ORGANISM: Artificial
<220> FEATURE:
<223> OTHER INFORMATION: PCT oligonucleotide primer

<400> SEQUENCE: 19
ggtcggacat tcctgcttta                                              20

<210> SEQ ID NO 20
<211> LENGTH: 20
<212> TYPE: DNA
<213> ORGANISM: Artificial
<220> FEATURE:
<223> OTHER INFORMATION: PCT oligonucleotide primer

<400> SEQUENCE: 20
gatatgcggt ccctactcca                                              20

<210> SEQ ID NO 21
<211> LENGTH: 20
<212> TYPE: DNA
<213> ORGANISM: Artificial
<220> FEATURE:
<223> OTHER INFORMATION: PCT oligonucleotide primer

<400> SEQUENCE: 21
tggggtacaa gaggcttcag                                              20
```

```
<210> SEQ ID NO 22
<211> LENGTH: 20
<212> TYPE: DNA
<213> ORGANISM: Artificial
<220> FEATURE:
<223> OTHER INFORMATION: PCT oligonucleotide primer

<400> SEQUENCE: 22
tacaggagtg gggacaggaa                                              20

<210> SEQ ID NO 23
<211> LENGTH: 20
<212> TYPE: DNA
<213> ORGANISM: Artificial
<220> FEATURE:
<223> OTHER INFORMATION: PCT oligonucleotide primer

<400> SEQUENCE: 23
gttctctggc tggaacacct                                              20

<210> SEQ ID NO 24
<211> LENGTH: 20
<212> TYPE: DNA
<213> ORGANISM: Artificial
<220> FEATURE:
<223> OTHER INFORMATION: PCT oligonucleotide primer

<400> SEQUENCE: 24
ccccatcacc tgcagaaata                                              20

<210> SEQ ID NO 25
<211> LENGTH: 20
<212> TYPE: DNA
<213> ORGANISM: Artificial
<220> FEATURE:
<223> OTHER INFORMATION: PCT oligonucleotide primer

<400> SEQUENCE: 25
ccacagggct attttgggta                                              20

<210> SEQ ID NO 26
<211> LENGTH: 20
<212> TYPE: DNA
<213> ORGANISM: Artificial
<220> FEATURE:
<223> OTHER INFORMATION: PCT oligonucleotide primer

<400> SEQUENCE: 26
gccatgccgt ttgtattctc                                              20

<210> SEQ ID NO 27
<211> LENGTH: 24
<212> TYPE: DNA
<213> ORGANISM: Artificial
<220> FEATURE:
<223> OTHER INFORMATION: PCT oligonucleotide primer

<400> SEQUENCE: 27
gggaggccat gctgtttgta ttct                                         24

<210> SEQ ID NO 28
<211> LENGTH: 24
<212> TYPE: DNA
```

```
<213> ORGANISM: Artificial
<220> FEATURE:
<223> OTHER INFORMATION: PCT oligonucleotide primer

<400> SEQUENCE: 28
aacagcagtt ctctggctgg aaca                                              24
```